(12) United States Patent
Schwartz et al.

(10) Patent No.: US 6,468,314 B2
(45) Date of Patent: Oct. 22, 2002

(54) CARTILAGE REPAIR UNIT

(75) Inventors: Robert E. Schwartz, Old Westbury; Daniel A. Grande, Seacliff, both of NY (US)

(73) Assignee: DePuy Orthopaedics, Inc., Warsaw, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/801,450

(22) Filed: Mar. 8, 2001

(65) Prior Publication Data

US 2001/0010023 A1 Jul. 26, 2001

Related U.S. Application Data

(63) Continuation of application No. 09/325,957, filed on Jun. 4, 1999, now Pat. No. 6,251,143.

(51) Int. Cl.$^7$ .................................................. A61F 2/02
(52) U.S. Cl. ................................ 623/23.72; 623/14.12
(58) Field of Search ................ 623/14.12, 23.72–23.74; 606/75

(56) References Cited

U.S. PATENT DOCUMENTS

| | | | |
|---|---|---|---|
| 3,978,862 A | 9/1976 | Morrison | |
| 4,884,572 A | 12/1989 | Bays et al. | |
| 4,895,148 A | 1/1990 | Bays et al. | |
| 4,904,259 A | 2/1990 | Itay | |
| 4,976,715 A | 12/1990 | Bays et al. | |
| 5,269,783 A | 12/1993 | Sander | |
| 5,270,300 A | 12/1993 | Hunziker | |
| 5,306,311 A | 4/1994 | Stone et al. | |
| 5,500,000 A | 3/1996 | Feagin et al. | |
| 5,624,463 A | 4/1997 | Stone et al. | |
| 5,632,745 A | 5/1997 | Schwartz | |
| 5,713,374 A | 2/1998 | Pachence et al. | |
| 5,728,102 A | 3/1998 | Feingold et al. | |
| 5,749,874 A | 5/1998 | Schwartz | |
| 5,769,899 A | 6/1998 | Schwartz et al. | |
| 5,993,475 A | 11/1999 | Lin et al. | |
| 6,080,194 A | 6/2000 | Pachence et al. | |
| 6,096,080 A | 8/2000 | Nicholson et al. | |
| 6,296,641 B2 * | 10/2001 | Burkhead et al. | 606/61 |

FOREIGN PATENT DOCUMENTS

| | | | |
|---|---|---|---|
| WO | PCT/US96/05551 | | 5/1996 |
| WO | PCT/US96/00451 | * | 7/1997 |
| WO | PCT/US97/02085 | * | 8/1997 |

\* cited by examiner

*Primary Examiner*—John J. Wilson
*Assistant Examiner*—Michael B. Priddy
(74) *Attorney, Agent, or Firm*—Barnes & Thornburg

(57) ABSTRACT

A bio-absorbable cartilage repair system is provided for regenerating damaged or destroyed articular cartilage on a joint surface of a bone by establishing a chondrogenic growth-supporting matrix between an area of damaged or destroyed articular cartilage that has been removed and an adjacent healthy area of articular cartilage and subchondral cancellous bone. The system is an assembly of a delivery unit and a porous insert. The delivery unit is formed of bio-absorbable material and configured and dimensioned to be mounted in both an area of damaged or destroyed articular cartilage that has been removed and an adjacent healthy area of articular cartilage and cancellous bone. The delivery unit has a central body and a plurality of radially extending, flexible support arms projecting outwardly from the central body and configured and dimensioned to support the insert at least partially thereover. The insert is supported by the delivery unit, formed of bio-absorbable material, and establishes communication between the removed area and the adjacent healthy area for a chondrogenic growth-supporting matrix.

45 Claims, 19 Drawing Sheets

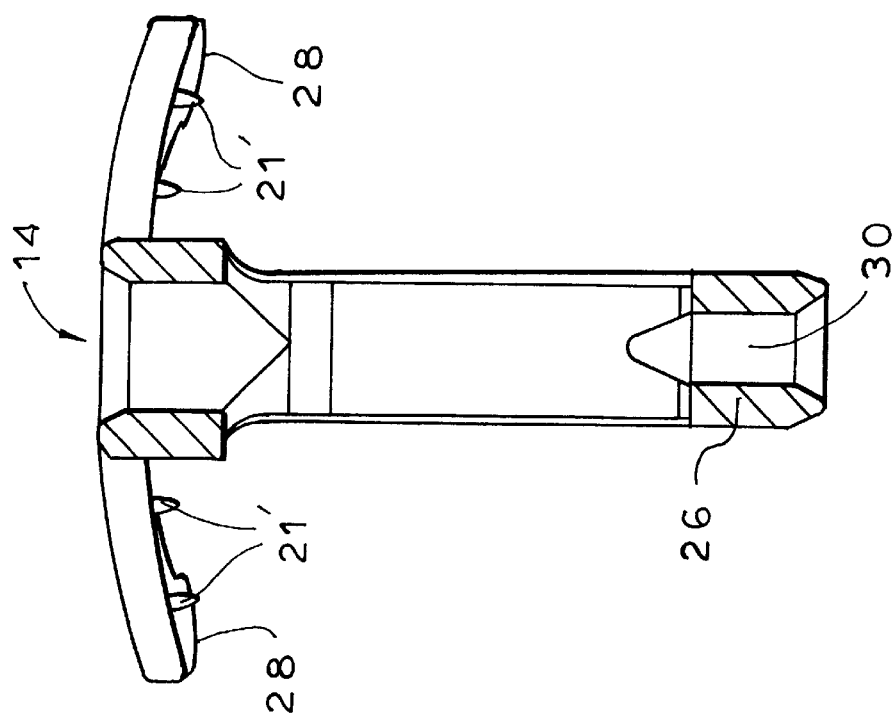
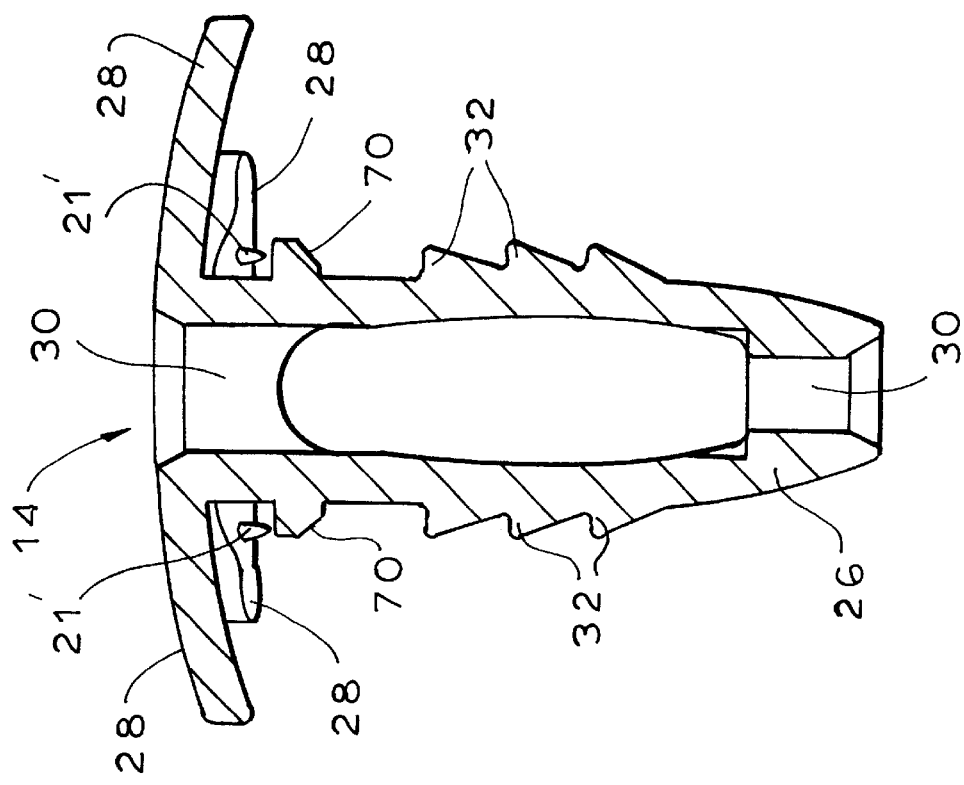

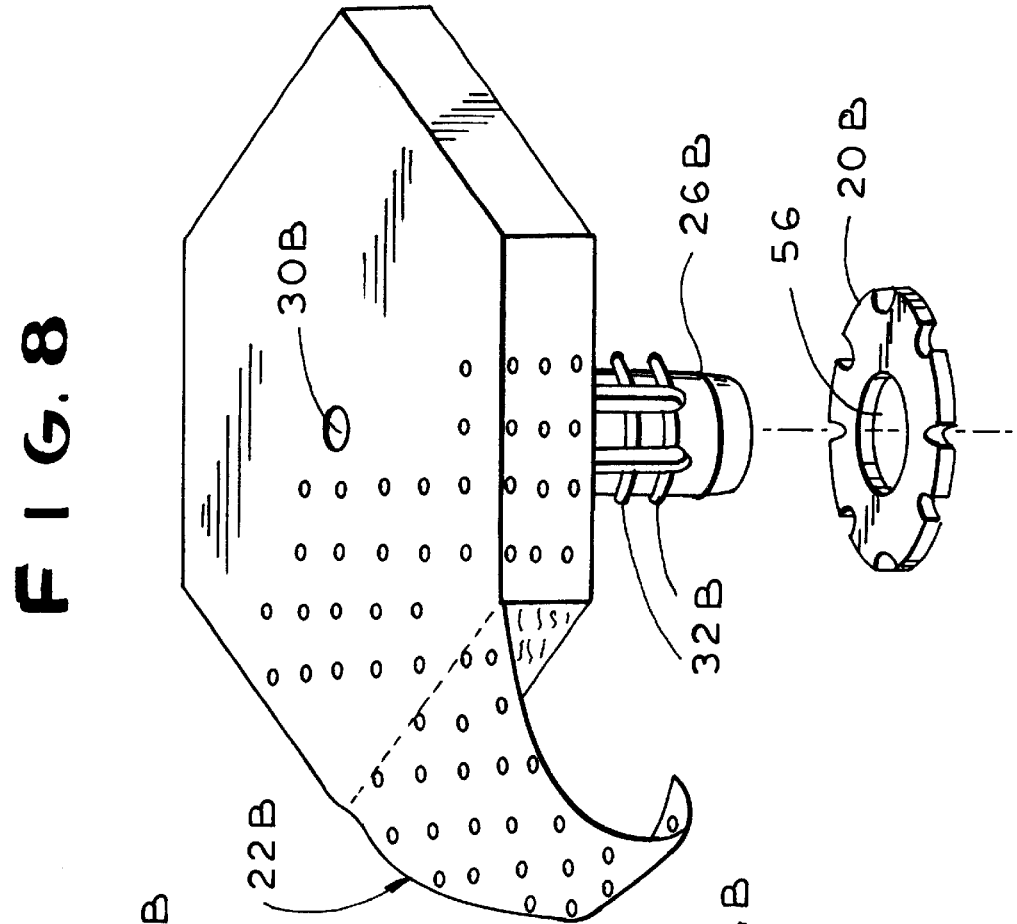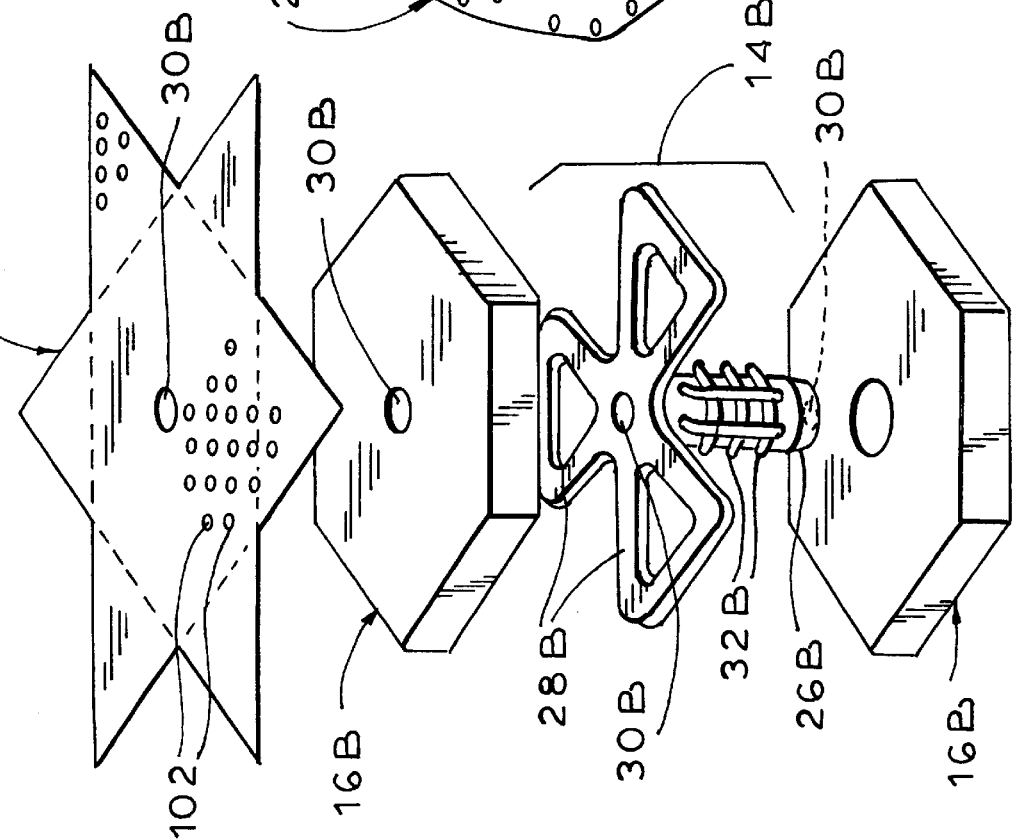

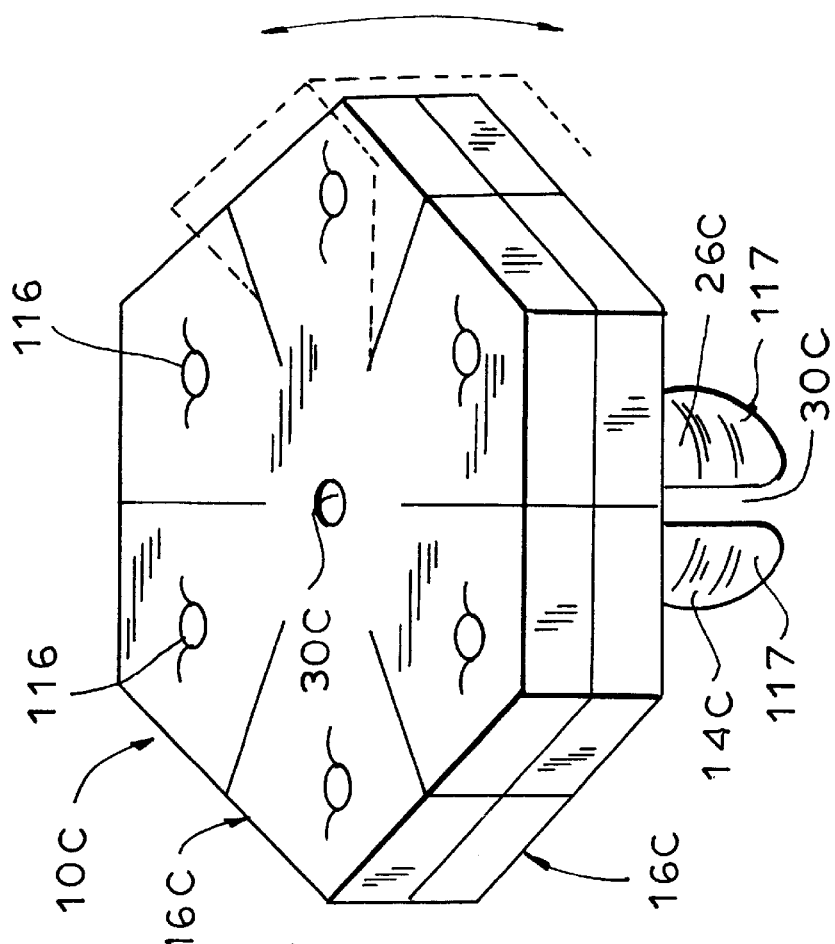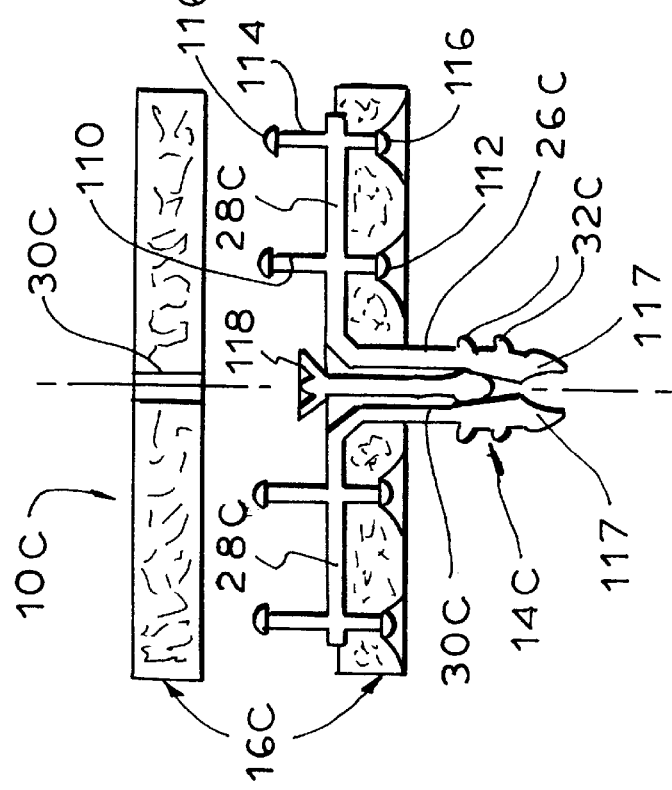

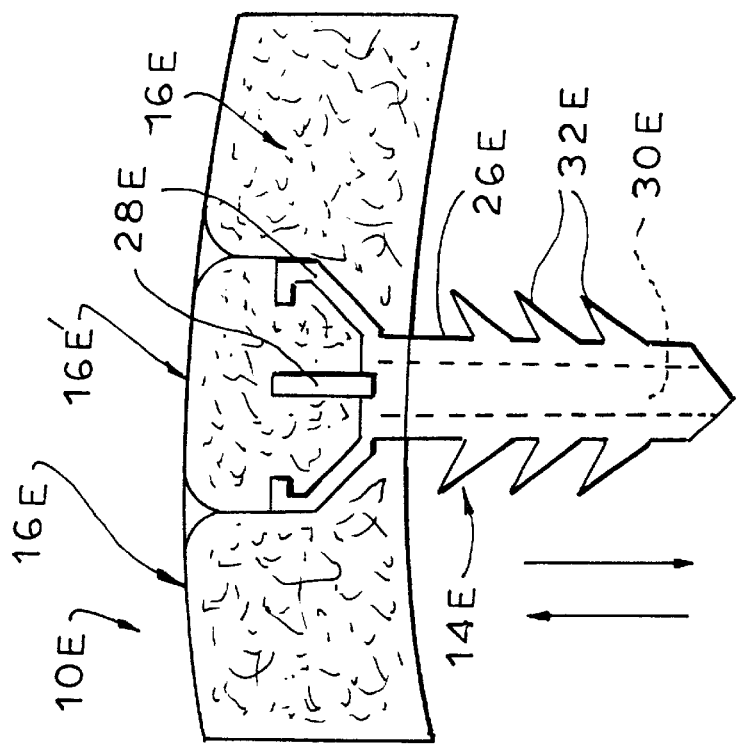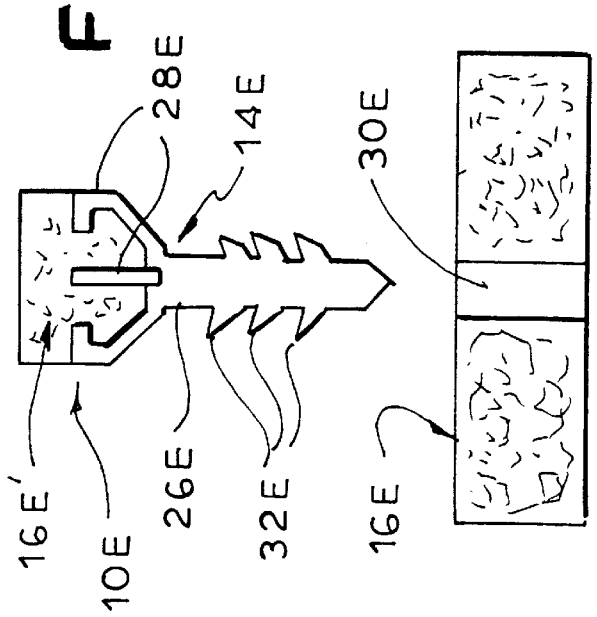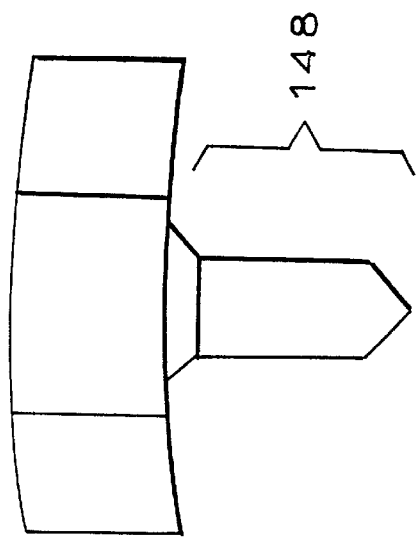

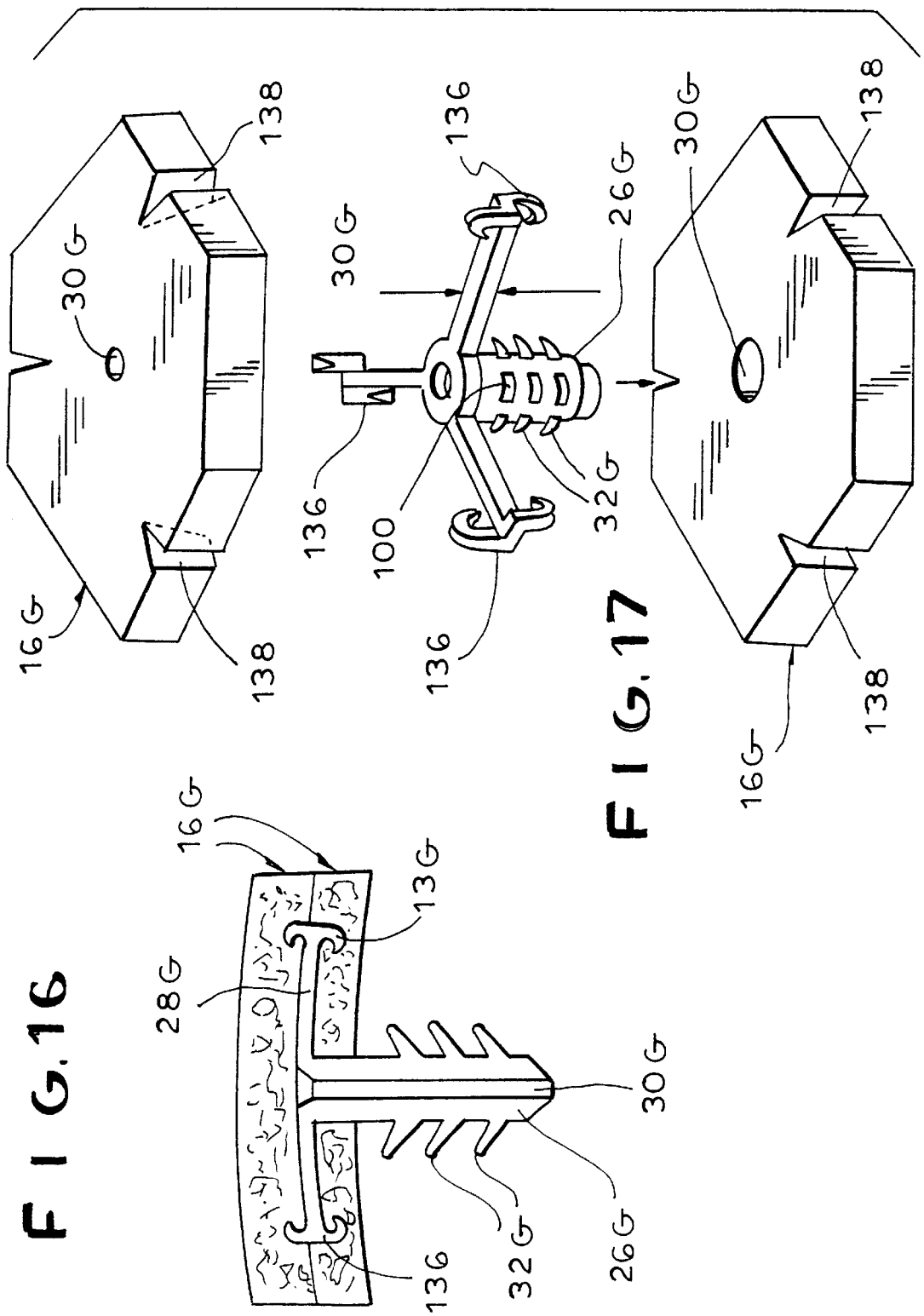

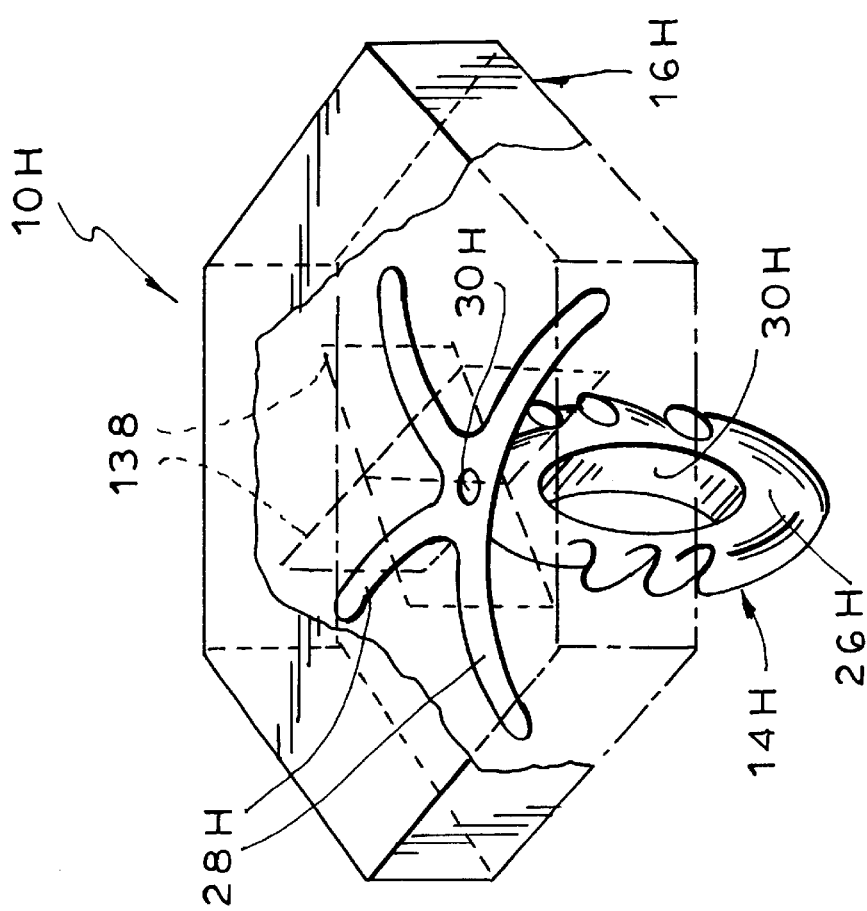
FIG. 18
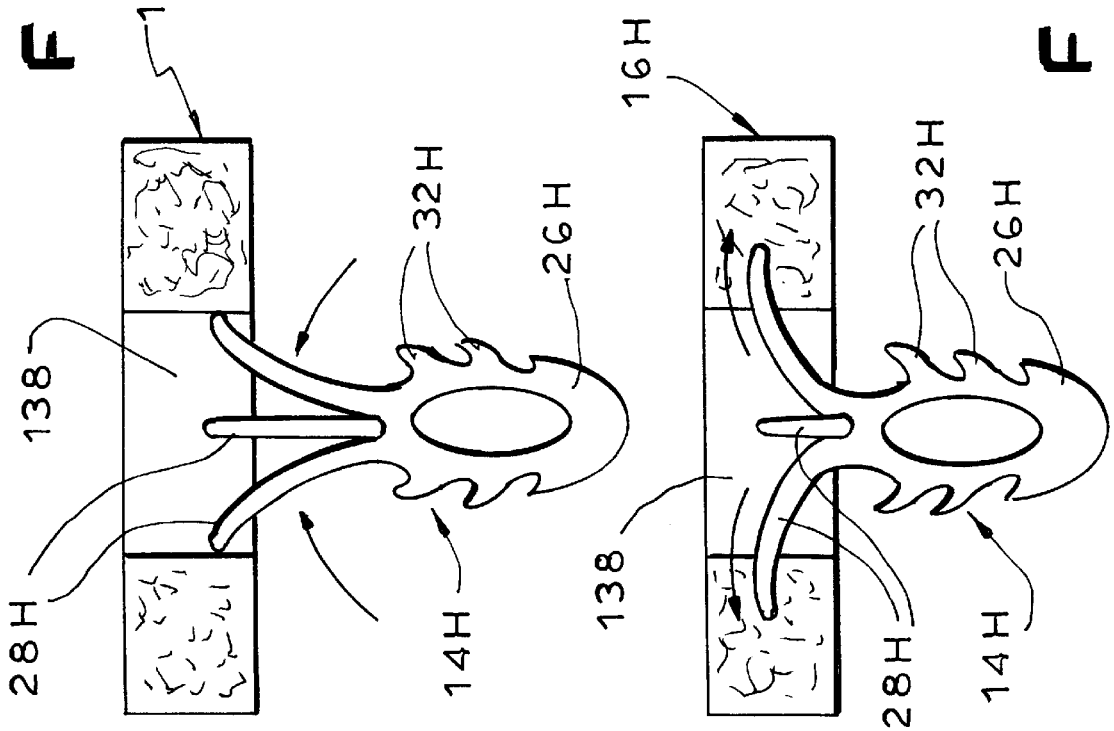
FIG. 19
FIG. 20

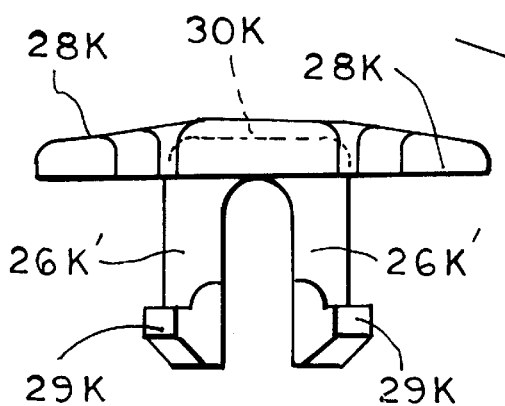
FIG. 26
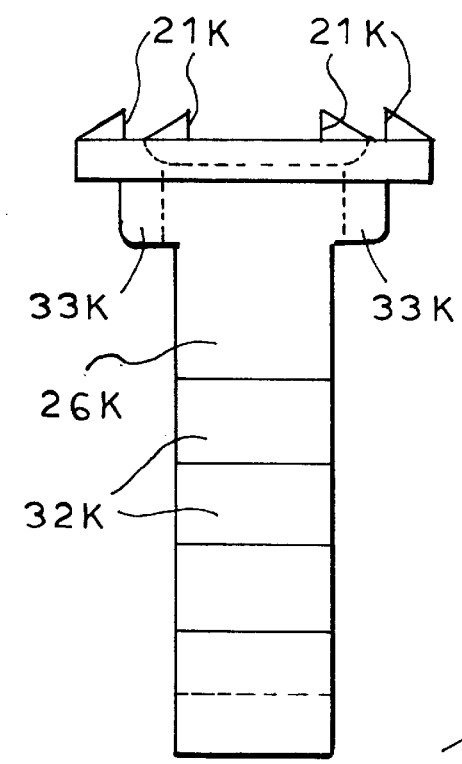
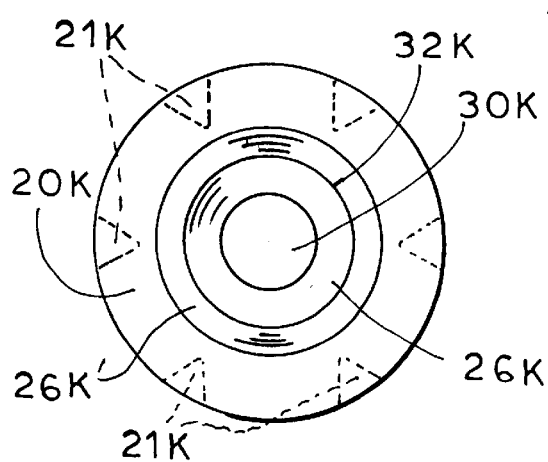
FIG. 27
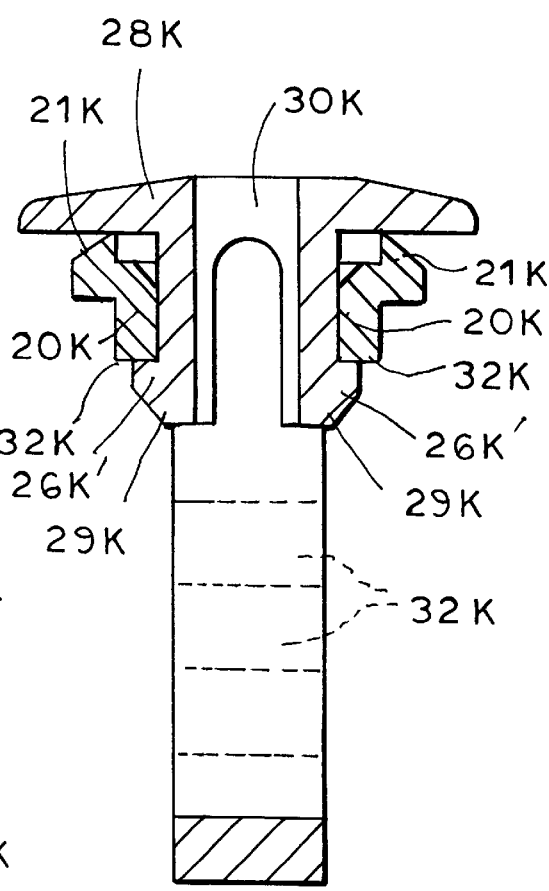
FIG. 28

FIG. 35
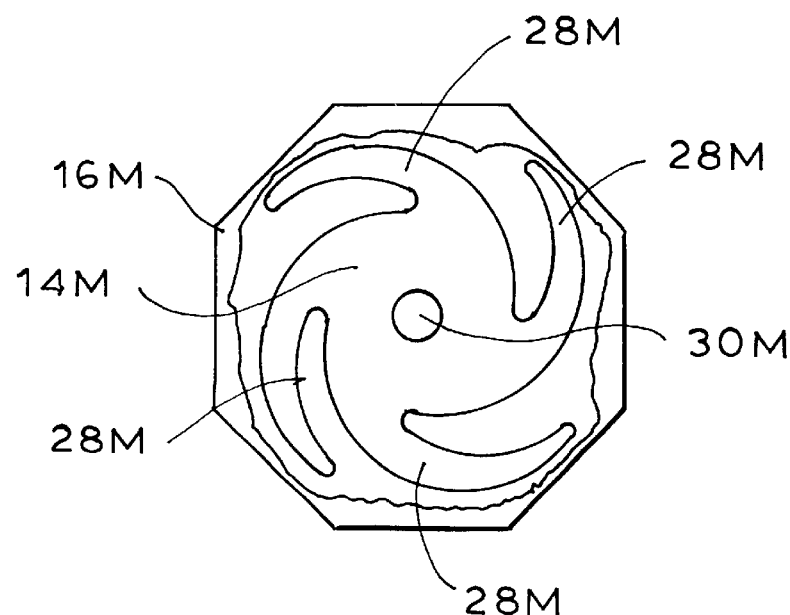
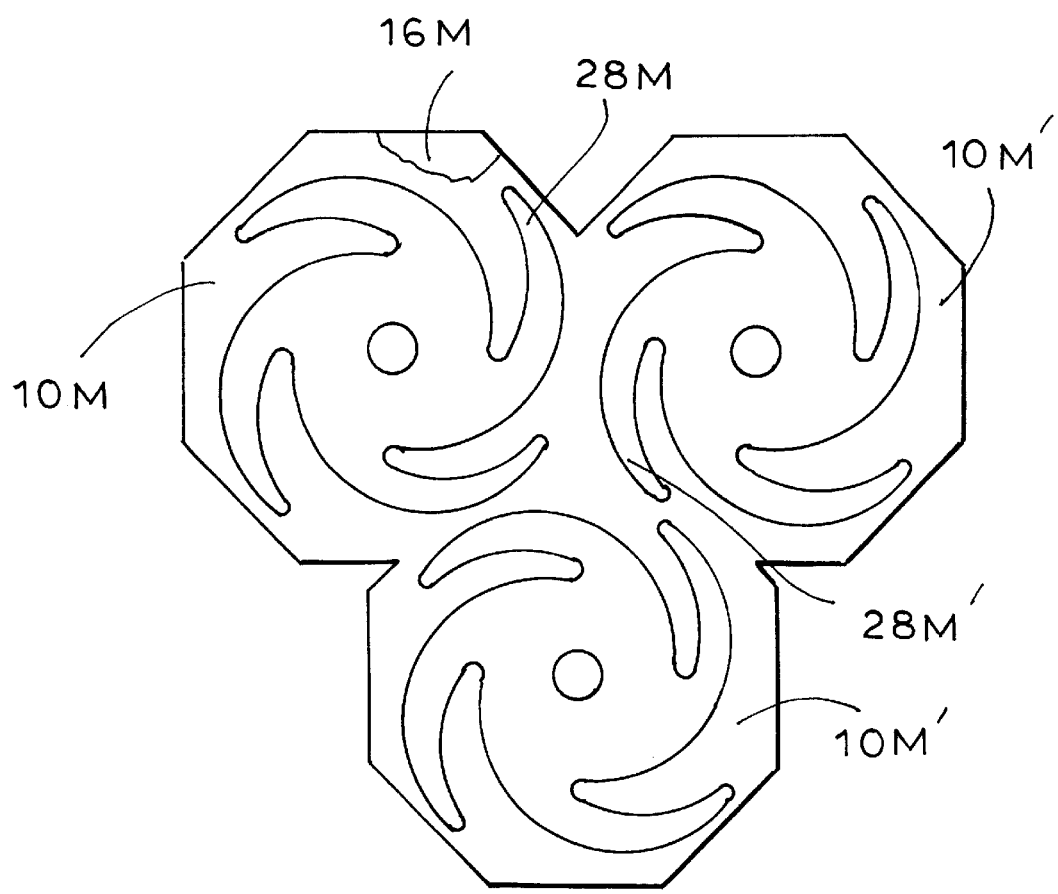
FIG. 36

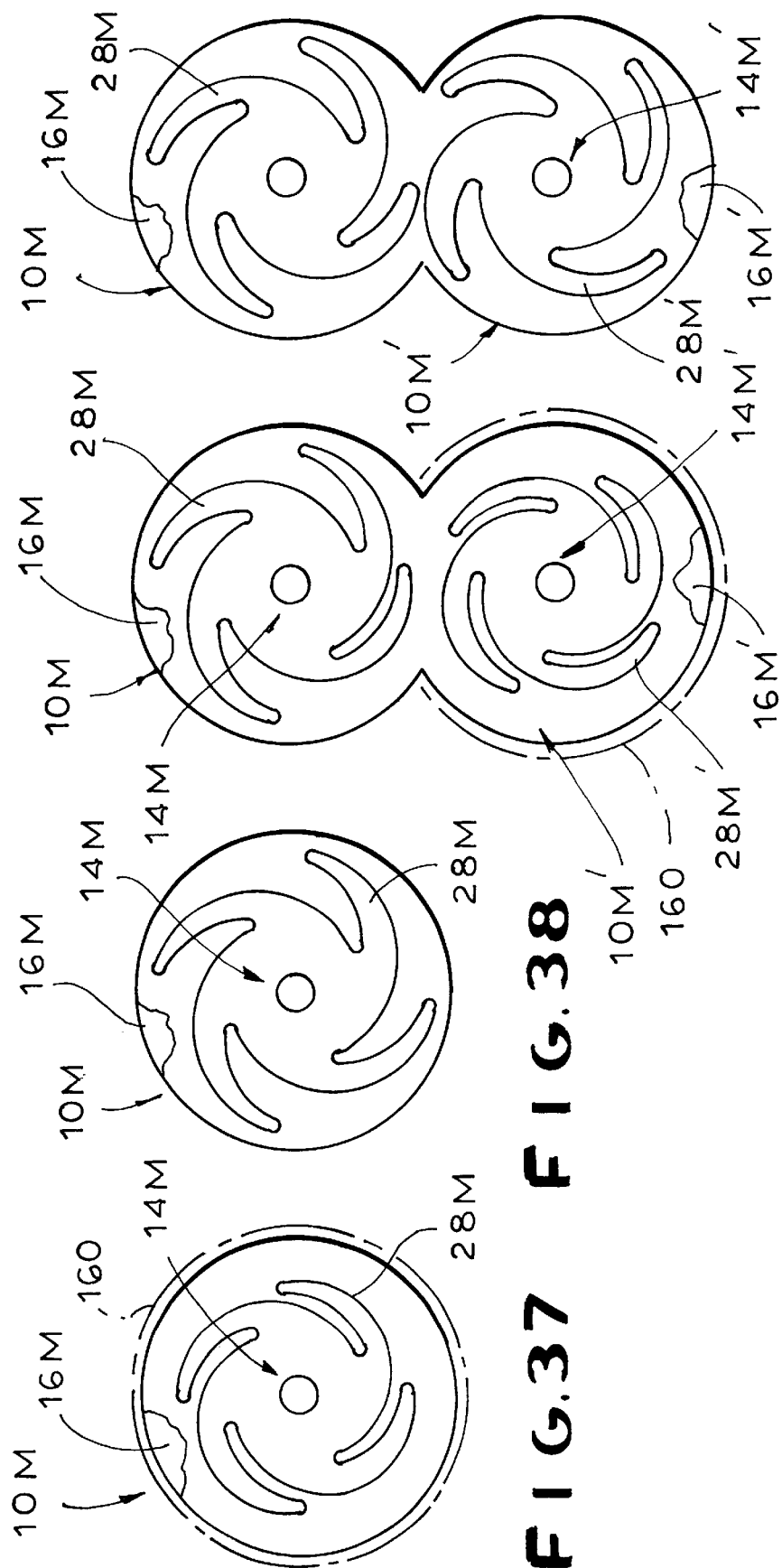

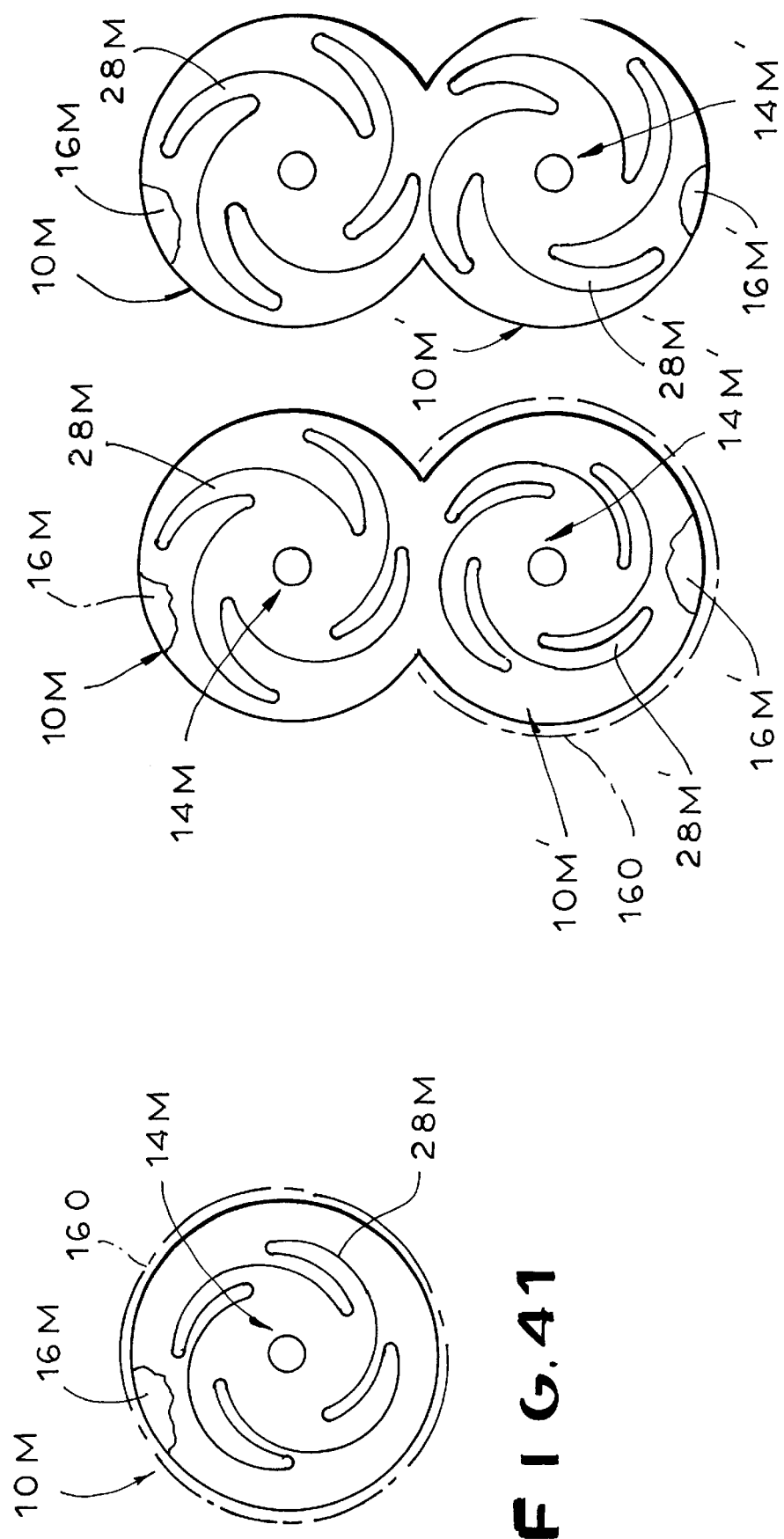

CARTILAGE REPAIR UNIT

CROSS-REFERENCE TO RELATED APPLICATIONS

This application is a continuation of U.S. application Ser. No. 09/325,957, filed Jun. 4, 1999 now U.S. Pat. No. 6,251,143.

BACKGROUND OF THE INVENTION

This invention relates to a bio-absorbable cartilage repair system for regenerating articular cartilage and, more particularly, a system which allows for vascular invasion and cellular migration between the system and the adjacent healthy area of articular cartilage and cancellous bone, thereby resulting in regeneration of the damaged articular cartilage.

Articular cartilage on the surface of bones in joints, most particularly the knee, ankle and hip joints, is susceptible to deterioration caused by injury or disease. This deterioration of cartilage leads to pain and eventually loss of joint movement and more severe pain. As a result, various methods have been developed to treat and repair damaged or destroyed articular cartilage.

Prosthetic devices are often used to replace damaged or destroyed articular cartilage. For example, U.S. Pat. No. 4,627,853 discloses prosthesis which are used for articular cartilage replacement. The prosthesis are prepared by demineralization of a bone segment, the demineralized bone segment serving as a replacement for articular cartilage.

U.S. Pat. No. 5,176,710 discloses a prosthesis for replacing bone material on the articulating surface of a joint. The prosthesis has a specific modulus of elasticity so as to confer stiffness to the prosthesis, and contains concave shapes which are suitable for biologic ingrowth.

U.S. Pat. No. 3,745,590 discloses a prosthesis for the repair or replacement of joints, which prosthesis comprises a body portion, including a stem and ligamentous elements, and allows for tissue ingrowth.

U.S. Pat. No. 5,123,927 discloses a knee prosthesis comprising bone cement containing an antibiotic.

U.S. Pat. No. 4,904,259 discloses a resorbable gel, including ex vivo chondrocyte cells, press fit into a cartilage defect.

U.S. Pat. No. 5,270,300 discloses a scaffold into which cells grow, but without any blood supply from the subchondral bone.

U.S. Pat. No. 5,306,311 discloses a resorbable prosthesis suitable for biologic ingrowth.

PCT Publication No. PCT/WO95/30383 discloses ex vivo proliferated, denuded chondrogenic cells for synthetic cartilage use in surgically repairing cartilage defects.

Although there are several prosthetic devices which can be used in the replacement of damaged or destroyed articular cartilage, prosthetic devices have several disadvantages. For example, cements which are used to attach prosthetic devices to bones may loosen and eventually fail. In addition, fragmented cement can move into the joints and associated lymph tissue and cause inflammation and further damage. Further, cements result in the formation of fibrous tissue between the bone and the prosthesis. Another major disadvantage associated with the use of prosthesis is that the prosthetic device may be larger than the damaged cartilage that needs to be replaced, thereby requiring removal of portions of healthy bone and/or cartilage in order to accommodate the prosthetic device. Hence, the need remains for a system for repairing and regenerating articular cartilage which avoids the problems associated with prosthetic devices.

Another means used to treat damaged articular cartilage is the placement of repair pieces onto the bone, which repair pieces substitute for cut-out pieces of cartilage. For example, U.S. Pat. No. 5,067,964 discloses an articular cartilage repair piece which comprises a layer of non-woven, felted fibrous material which is limp and readily conformable to flat and curved surfaces. The articular cartilage repair piece is attached to the bone, for example, by bio-absorbable screws or pins or like temporary fixation techniques. Fibrous tissue ingrowth eventually surrounds the repair piece thereby causing the repair piece to be permanently attached to the bone. Although U.S. Pat. No. 5,067,964 discloses an alternative method for repairing damaged articular cartilage, it does not disclose any means or method of regenerating damaged or destroyed articular cartilage. Hence, the need remains for a system for regenerating damaged or destroyed articular cartilage, wherein the regenerated articular cartilage is functionally similar to non-damaged articular cartilage.

Commonly owned U.S. Pat. Nos. U.S. Patent No. 5,632,745; U.S. Pat. No. 5,749,874; and U.S. Pat. No. 5,769,899 disclose such a regenerating system and are incorporated herein by reference. However, the regenerating systems disclosed therein have not proved to be entirely satisfactory from the points of view of both the manufacturer and the surgeon installing the same in a patient.

Accordingly, an object of this invention is to provide a system for regenerating articular cartilage.

Another object is to provide a system for regenerating articular cartilage wherein the regenerated articular cartilage is functionally superior to fibrous or fibrocartilagenous repairs and is functionally similar to non-damaged articular cartilage.

A further object is to provide a cartilage repair system for use in regenerating damaged or destroyed articular cartilage.

It is another object of the present invention to provide an embodiment of the cartilage repair system which does not employ cement or non-bio-absorbable prosthetic devices.

It is a further object to provide an embodiment of the cartilage repair system for repairing bone as well where there are injuries to both cartilage and bone.

SUMMARY OF THE INVENTION

It has now been found that the above and related objects of the present invention are obtained by a bio-absorbable cartilage repair system for regenerating damaged or destroyed articular cartilage on the joint surface of a bone, which system establishes a chondrogenic growth-supporting matrix between an area of damaged or destroyed articular cartilage that has been removed and an adjacent healthy area of articular cartilage and cancellous or trabecular bone. The system comprises an assembly of a bio-absorbable delivery unit and a porous bio-absorbable insert. The delivery unit is formed of bio-absorbable material and configured and dimensioned to be mounted in both an area of damaged or destroyed articular cartilage that has been removed and an adjacent healthy area of articular cartilage and cancellous bone. The delivery unit has a central body and a plurality of radially extending, flexible support arms projecting outwardly from the central body and configured and dimensioned to support the insert at least partially thereover. The insert is supported by the delivery unit, formed of bioabsorbable material, and establishes communication between the removed area and the adjacent healthy area for a chondrogenic growth-supporting matrix.

In a preferred embodiment, the insert is disposed on the upper, lower, and outer surfaces of the support arms, and the support arms have free ends circumferentially spaced from one another to define areas for receipt of a chondrogenic growth-supporting matrix. The support arms preferably have circumferentially spaced free ends adapted to engage and at least partially spatially stabilize the insert. The support arm free ends may be horizontally or vertically barbed. The central body adjacent a bottom end thereof defines a plurality of outwardly extending flanges.

In a preferred embodiment, the insert has a top, a bottom and a sidewall connecting the top and bottom. The bottom allows vascular invasion therethrough, and the top and sidewall allow cellular migration therethrough by an adjacent healthy area of articular cartilage and subchondral cancellous bone. The insert may include cells to facilitate establishing such communication. The sidewall is preferably polygonal in plan. Each of the delivery unit and the insert preferably essentially consists of completely bio-absorbable material which is ceramic-free and dimensionally stable in synovial joint fluid against expansion due to the absorption thereof.

The system may additionally include retainer means for securing the insert to the delivery unit. The retainer means is secured to a portion of the central body below the insert and bears upwardly against the insert. The retainer means essentially consists of completely bio-absorbable material which is ceramic-free and dimensionally stable in synovial joint fluid against expansion due to the absorption thereof.

Preferably the system additionally includes a porous film formed of bio-absorbable material securing the insert to the delivery unit. The porous film has a central film portion disposed over the insert and a plurality of film fingers projecting outwardly from the central film portion, downwardly and inwardly, under the support arms. Optionally, upwardly barbed retainer means are secured to the central body and bear upwardly against the film fingers. The porous film essentially consists of completely bio-absorbable material which is ceramic-free and dimensionally stable in synovial joint fluid against expansion due to the absorption thereof.

In another preferred embodiment, the insert is a flexible porous film formed of bio-absorbable material secured to the delivery unit. The porous film has a central film portion disposed over the support arms and a plurality of film fingers projecting outwardly from the central film portion, downwardly and inwardly, under the support arms. A retainer means is preferably secured to the central body and bears upwardly against the film fingers. The porous film essentially consists of completely bio-absorbable material which is ceramic-free and dimensionally stable in synovial joint fluid against expansion due to the absorption thereof.

In the latter embodiment, preferably the central body defines an aperture extending longitudinally therethrough, and the insert defines an aperture extending longitudinally therethrough. A retainer means may be secured to the central body and bears upwardly against the insert, the retainer body defining an aperture extending longitudinally therethrough coaxial with the central body aperture. A porous film consisting substantially of completely bio-absorbable material may secure the insert to the delivery unit, the porous film defining an aperture extending longitudinally therethrough coaxial with the central body aperture. When the insert is a flexible porous film consisting substantially of completely bio-absorbable material secured to the delivery unit, the porous film may define an aperture extending longitudinally therethrough coaxial with the central body aperture.

In yet another embodiment, at least a portion of the delivery unit central body disposed below the insert defines flexible legs, the system additionally including means for moving the legs from a horizontally retracted orientation enabling removal of the assembly to a horizontally expanded orientation fixing the assembly in place. Preferably, the flexible legs are resilient, and the moving means is retractable to enable movement of the legs from the expanded orientation to the retracted orientation.

Preferably, the insert consists substantially of a bio-absorbable material selected from the group consisting of hyaluronic acid, polyglycolic acid, collagen, polylactic acid, fibrin clot, periosteal cells, polydioxane, polyester, alginate and combinations thereof, while the delivery unit comprises a bio-absorbable material selected from the group consisting of hyaluronic acid polyglycolic acid, polylactic acid, alginate and combinations thereof.

In a preferred embodiment, the insert includes a repair factor releasably disposed in the insert to assist in establishing the chondrogenic growth-supporting matrix. The repair factor may be a growth factor, preferably one selected from the group consisting of fibroblast growth factor, transforming growth factor beta, insulin, insulin like growth factor, platelet derived growth factor and combinations thereof. Alternatively, the repair factor may be an attachment factor, preferably one selected from the group consisting of fibronectin, RGD polypeptide and combinations thereof, or a cell factor, preferably one selected from the group consisting of stem cells, periosteal cells, and cells containing genes specific for cartilage formation and combinations thereof. Indeed, the repair factor preferably includes growth, attachment and cell factors.

The delivery units of the assemblies are disposed within the bone and the removed area, and the inserts of the assemblies establish the chondrogenic growth-supporting matrix over a substantial portion of the removed area. The insert of the assemblies may be polygonal in configuration and interfitting.

The cartilage repair system preferably includes means precluding relative rotation of the delivery unit and the insert in the delivery unit.

The present invention further encompasses a cartilage repair system adapted to be mounted on the joint surface of a bone to establish a chondrogenic growth-supporting matrix, wherein the system comprises a bio-absorbable delivery unit configured and dimensioned to be mounted on the bone, the unit including a support frame and means for mounting the unit in the bone, and a porous bio-absorbable insert supported by the support frame to provide a chondrogenic growth-supporting matrix. Preferably the support frame is constructed to allow vascular invasion and cellular migration to the insert.

In one preferred embodiment of the present invention, the delivery unit is a subassembly of two separately formed components, one of the components being configured and dimensioned to be mounted in both an area of damaged or destroyed articular cartilage that has been removed and an adjacent healthy area of articular cartilage and cancellous bone, and the other component having a central body and a plurality of radially extending, flexible support arms projecting outwardly from the central body and configured and dimensioned to support the insert at least partially thereover.

Preferably, the one of the components defines a longitudinal aperture therethrough and the central body of the other component is configured and dimensioned to at least partially pass through the aperture. The subassembly may be assembled with the insert prior to use. At least one of the components includes means for retaining the components together after assembly, and the subassembly includes retainer means for bearing on a portion of the insert intermediate the two components to lock the delivery unit portion in place.

Additionally, the present invention encompasses a bioabsorbable cartilage repair system comprising an assembly consisting essentially of two delivery units and a single flexible porous insert. The insert is supported by both of the delivery units, is formed of flexible bio-absorbable material, and establishes communication between the removed area and the adjacent healthy area for a chondrogenic growth-supporting matrix. The delivery units are configured and dimensioned to enable them to be disposed along a common longitudinal axis, facing each other, and connected only by the insert for insertion into a patient. The assembly is then unfolded to enable the delivery units to be separately mounted along generally parallel longitudinal axes, side-by-side. Preferably the insert defines a pair of insert portions, each insert portion extending over the top of a respective one of the delivery units, and a connecting portion of reduced width foldably connecting the insert portions together.

Further, the present invention encompasses a bioabsorbable cartilage repair system comprising an assembly of a delivery unit and a porous insert. The delivery unit has a central body and an inwardly compressible plurality of spirally or helically extending, flexible support arms projecting outwardly from the central body and configured and dimensioned to support the insert at least partially thereover. Preferably, the system comprises at least two of the assemblies, each delivery unit being mounted side-by-side such that at least one support arm of one of the delivery units inwardly compresses at least one support arm of the other of the delivery units. The at least one support arm of one unit would overlap at least one support arm of the other unit if at least one support arm were not inwardly compressed.

In a preferred embodiment of the present invention, a top layer of the insert contains a chondrogenic growth-supporting matrix, and a lower portion of the insert contains an osteogenic growth-supporting matrix, the assembly being configured and dimensioned to be disposed with the chondrogenic growth-supporting matrix adjacent a healthy area of articular cartilage and the osteogenic growth-supporting matrix adjacent a healthy area of subchondral cancellous bone, thereby to establish chondrogenic and osteogenic growth-supporting matrices in removed areas of damaged or destroyed articular cartilage and subchondral bone, respectively.

In another preferred embodiment, the delivery unit includes a head portion and a stem portion, the head and stem portions being pivotally joined together, one of the portions preferably defining a ball and the other of the portions preferably defining a socket. Optimally the stem portion defines a ball at a distal end, and the head portion defines a socket at a proximal end, the ball being pivotally maintained in the socket such that the head portion is pivotable relative to the stem portion.

BRIEF DESCRIPTION OF THE DRAWING

The above brief description, as well as further objects, features and advantages of the present invention, will be more fully understood by reference to the following detailed description of the presently preferred, albeit illustrative, embodiments of the present invention when taken in conjunction with the accompanying drawings wherein:

FIG. 4 is a sectional view thereof taken along the line 4—4 of FIG. 3;

FIG. 5 is a sectional view thereof taken along the line 5—5 of FIG. 3;

FIG. 7 is a fragmentary exploded isometric view of a third embodiment;

FIG. 8 is a partially exploded isometric view of the third embodiment;

FIG. 9 is a partially exploded sectional view of a fourth embodiment;

FIG. 10 is an isometric assembly view of the fourth embodiment;

FIG. 13A is an exploded side elevational view, partially in cross-section of a sixth embodiment;

FIG. 13B is a side elevational assembly view of the sixth embodiment;

FIG. 16 is a side elevational view, partially in cross-section, of an eighth embodiment;

FIG. 17 is an exploded isometric view of the eighth embodiment;

FIG. 18 is a side elevational view, partially in cross-section, of a ninth embodiment, with the insert being inserted into the delivery unit;

FIG. 19 is a view similar to FIG. 18, but shows the insert fully inserted into the delivery unit;

FIG. 20 is an isometric assembly view of the ninth embodiment;

FIG. 26 is an exploded side elevational view of the eleventh embodiment with the insert being removed for pedagogic purposes;

FIG. 27 is a bottom plan view of the lower portion of the assembly of FIG. 26;

FIG. 28 is a side elevation assembly view of the eleventh embodiment, partially in cross section;

FIG. 35 is a top plan view of a thirteenth or compressible arm embodiment, with portions of the insert cut away to reveal details of internal construction;

FIG. 36 is a top plan view of three assemblies of the thirteenth embodiment in contiguous relationship with portions of the insert partially cut away;

FIGS. 37–40 are schematic top plan views illustrating the method of installing contiguous assemblies of a variant of the thirteenth embodiment into a work area, with the compression tubing used in the method illustrated in phantom line and with portions of the insert partially cut away;

FIGS. 41–42 are schematic top plan views illustrating an alternative method of installing contiguous embodiments;

FIG. 43 is a top plan view of a variant of the thirteenth embodiment, with portions of the insert partially cut away;

Figure 1:
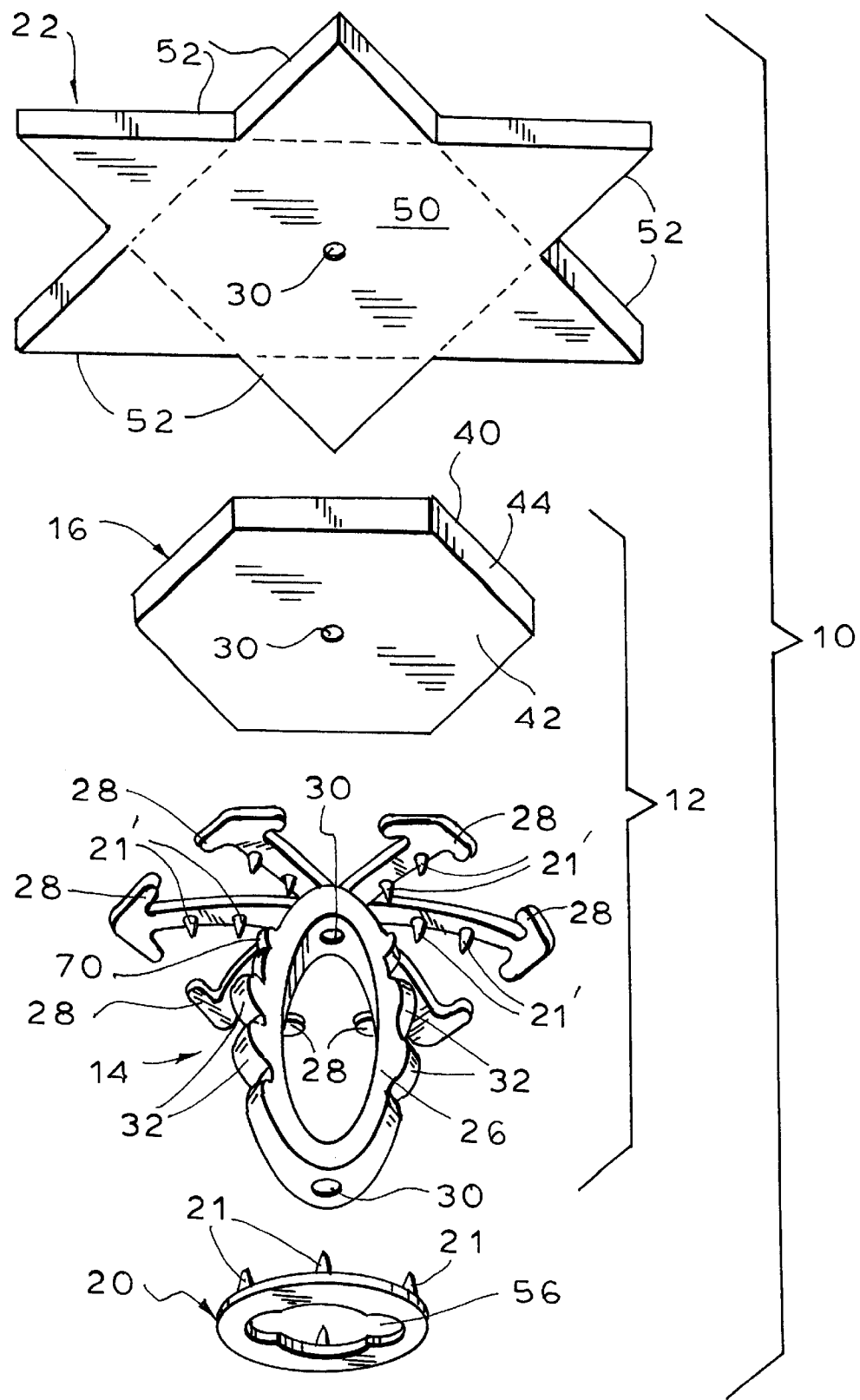
FIG. 1 is an exploded isometric view of a first embodiment of the assembly of the cartilage repair system.
Figure 2:
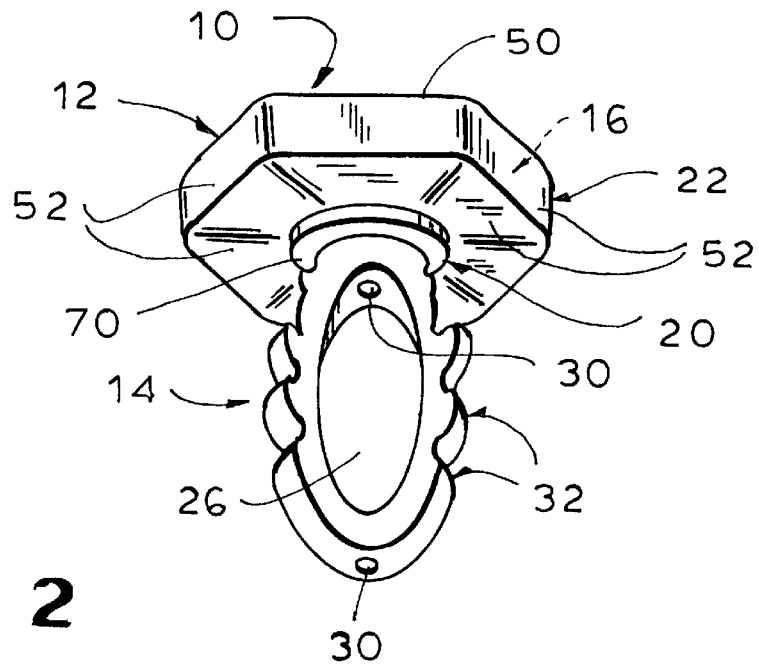
FIG. 2 is an isometric assembly view thereof.
Figure 3:
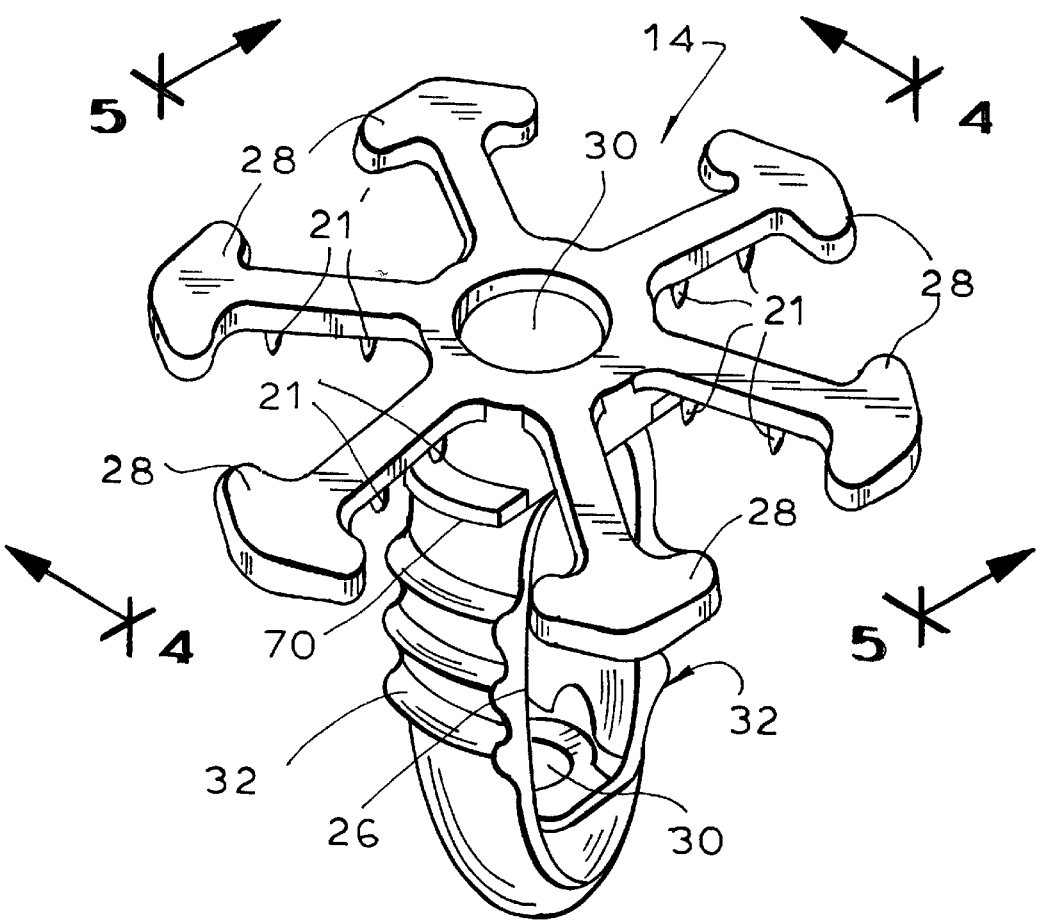
FIG. 3 is an isometric view of the delivery unit alone.

It will be appreciated that in various views (e.g., FIGS. 15, 20, 23, 24 and 35–44) the insert has been partially cut away in order to reveal details of internal construction.

Elements of the several embodiments which have the same or like structure and/or perform the same or like functions are identified by the same reference numerals. For composite reference identifications, the upper case following the reference numeral indicates the embodiment.

DETAILED DESCRIPTION OF THE PREFERRED EMBODIMENTS

Referring now to the drawing, and in particular to FIGS. 1–5 thereof, therein illustrated is a preferred first embodiment of a cartilage repair system according to the present invention, generally designated by the reference numeral 10. More particularly, the preferred cartilage repair system 10 is comprised of an assembly generally designated 12 (one being illustrated, but it being understood that the requisite number is determined by the extent of the damaged area). Each assembly 12 is in turn comprised of a bio-absorbable delivery unit 14 (seen alone in FIGS. 3–5) and a porous bio-absorbable insert 16 (seen with the delivery unit 14 in FIGS. 1 and 2). The delivery unit 14 is configured and dimensioned to be mounted in both the area from which damaged or destroyed articular cartilage has been removed and the adjacent healthy cancellous bone area of the bone. The porous insert 16 is supported by the delivery unit 14 and establishes communication between the removed area (that is, the area from which the damaged or destroyed articular cartilage has been removed) and the adjacent healthy area for a chondrogenic growth-supporting matrix, thereby promoting vascular invasion and cellular migration to achieve articular cartilage regeneration.

While the system 10 is discussed herein as being used to regenerate damaged or destroyed articular cartilage on the femoral knee joint surface K, those skilled in the medical arts will readily appreciate that the system 10 is equally useful in other articular joints such as the shoulder, hip, and the like. The extent of the damaged or destroyed articular cartilage on the surface of the bone will determine whether the system 10 employs a single assembly 12 or a plurality of assemblies 12. The illustrated assembly 12 (and in particular the delivery unit 14 thereof) is polygonal in plan and interfitting—that is, disposed such that two assemblies 12 can be mounted in contiguous abutting contact in a side-by-side relationship. The polygonal nature of the periphery of the assemblies permits interfitting of the assemblies 12 and is thus preferred where a plurality of the assemblies 12 are to be used to completely cover or tile a designated area of the bone. However, where only a single assembly 12 will be used, other configurations, such as a circular configuration, may be preferred.

While theoretically it might be possible to create in a single manufacturing operation (e.g., one employing photolithography) a unitary, one-piece, integral assembly 12 which performs the functions of both the delivery unit 14 and the insert 16, the present invention preferably utilizes at least two separate and independently formed components—namely, the delivery unit 14 and the insert 16. As will be discussed below in detail, the insert 16 can be made of a relatively wide variety of different materials and may even include a repair factor (such as a growth factor or an attachment factor) releasably disposed therein to assist in establishing the chondrogenic growth-supporting matrix.

Accordingly, the two-component nature of the assembly 12 of the present invention enables the insert 16 to be selected from a supply of different inserts 16 at the time of surgery so as to meet the particular needs of the patient at the time with regard to the basic composition of the insert 16 and any repair factor composition therein. Again, because of the differing natures of the insert 16 (and any repair factors therein) and its delivery unit 14, it may be necessary for particular types of inserts 16 to be stored before use in different environments from the delivery units 14—for example, in order to provide appropriate preservation of the repair factor. Finally, the delivery unit 14 and insert 16 of an assembly 12 must have different functional characteristics which would be difficult to achieve through known manufacturing techniques in an integral, one-piece, unitary element. Thus, as will be discussed below, the delivery unit 14 must have sufficient strength and integrity to enable it to be tamped into the bone without significant bending or deforming, while the insert 16 is preferably a flexible porous material in the form of a matrix to enable it to fit onto the delivery unit 14 and thereby provide a chondrogenic growth-supporting matrix positioned by the delivery unit 14.

The system 10 includes, in addition to the assembly 12, a retainer means generally designated 20 and a porous film generally designated 22.

The delivery unit 14 is formed of bio-absorbable material as configured and dimensioned to be mounted in both an area of damaged or destroyed articular cartilage that has been removed and an adjacent healthy area of articular cartilage and cancellous bone. The delivery unit 14 has an elongate central body 26 and a plurality of radially extending flexible support arms 28 projecting outwardly from the central body (or at least the longitudinal axis passing through the central body).. The arms 28 are configured and dimensioned to support the insert 16 laterally thereabout, at least partially thereover, and, optionally, therebelow. As illustrated in the first embodiment, the support arms 28 have free ends circumferentially spaced from one another to define areas for receipt of a chondrogenic growth-supporting matrix. Further, the support arms 28 have circumferentially spaced free ends adapted to engage and at least partially stabilize the insert 16. The support arms 28 are horizontally barbed to assist in retaining the insert in place on the delivery unit 14. (Alternatively, as illustrated in other embodiments, the support arm free ends may be vertically barbed.)

For reasons which will become apparent hereinafter, the elongate body 26 of the delivery unit 14 is preferably oval in shape, with the outer surface of the oval defining outwardly projecting steps 32 for engaging bone.

As illustrated, the delivery unit 14 has six support arms 28 regularly spaced about the central axis thereof, although clearly greater or lesser numbers of arms may be used.

The insert 16 is preferably hexagonally shaped, with the number of its sides matching the number of radial arms 28 of the delivery unit 14. Clearly, a greater or lesser number of sides may be defined by the insert 16, although preferably the number of sides is always equal to the number of radial arms 28. The insert 16 is preferably disposed in the first embodiment on the upper, lower and outer surfaces of the support arms 28. The insert 16 has a top 40, a bottom 42, and a sidewall 44 connecting the top 40 and bottom 42. The bottom 42 allows vascular invasion and cellular migration therethrough while the top 40 and sidewall 44 allow cellular migration therethrough by an adjacent healthy area of articular cartilage and subchondral cancellous bone. Preferably, the sidewall 44 is polygonal in plan to enable a plurality of the systems to be used in close proximity to occupy an enlarged area of damaged or destroyed articular cartilage that has been removed.

The first embodiment of the system 10 additionally includes a porous film 22 formed of bio-absorbable material for securing the insert 16 to the delivery unit 14. More particularly, the porous film 22 has a central film portion 50 disposed over the insert 16 and a plurality of film fingers 52 projecting outwardly from the central film portion 50 and being wrapped downwardly and inwardly under the support arms 28. Preferably, the porous film 22 has a plurality of film fingers 52 equal to the number of sides of the insert 16 and thus the number of radial arms 28.

The first embodiment of the system additionally includes a retainer 20 secured to the central body 26 and bearing upwardly against the film fingers 52, thereby to maintain the film 22 in position to maintain the insert 16 on the delivery unit 14. The central aperture 56 of retainer 20 is enlarged and elongated to enable passage of the retainer 20 over the outwardly extending steps 32 and locking flange 70 of the central body 26. Subsequent rotation of the retainer 20 about 90° locks the retaining means 20 in place against the film fingers 52. Alternatively, instead of rotation, one of the bottom surface of the film fingers 52 and the top surface of the retainer 20 is barbed so that it engages the other when the retainer 20 and fingers 52 approach.

In the preferred embodiment illustrated, the upper surface of the retainer 20 defines a plurality of upwardly extending barbs 21, and the bottom surface of each support arm 28 defines one or more downwardly extending barbs 21'. Such an arrangement securely locks the film fingers 52 wrapped under the support arms 28 in place between the retainer 20 and support arms 28, thereby to prevent accidental dislodgment thereof. Clearly, the upwardly directed barbs 21 may be used apart from the downwardly directed barbs 21', and vice versa.

It will be appreciated that each of the delivery unit 14, insert 16, porous film 22 and retainer 20 essentially consists of substantially completely bio-absorbable material which is dimensionally stable in synovial joint fluid against expansion due to the absorption thereof. Such material excludes ceramics and the like.

Each of the delivery unit 14, the insert 16, the retainer 20 and the porous film 22 defines one or more aligned small apertures or bores 30 extending therethrough along a central longitudinal axis to enable use of the system with a guidewire. As illustrated, the small aperture or bore 30 in the retainer 20 is part of a larger central aperture 56 and cannot be separately seen.

It will be appreciated that, even though the porous film 22 is illustrated as containing an aperture or bore 30 aligned with the apertures or bores 30 of the insert 16 and the delivery unit 14, in fact the porous film 22 may be imperforate with the task of creating an aperture or bore 30 therein being left to the surgeon. When the system 10 is assembled, the bore 30 passes through the porous film 22, sub-assembly of radial arms 28, central body 26 and retainer 20.

In order to enable the insert 16 to function as a chondrogenic growth-supporting matrix, it must have access to vascular invasion and cellular migration to regenerate the articular cartilage defect. Such access is provided on the internal periphery of the insert 16 by the bore 30 and on the external periphery of the insert 16 by the porous film 22 on the support arms 28. The porous film 22 enables indirect contact of the insert 16 with the adjacent healthy articular cartilage or with any adjacent repair assemblies 10. The porous film 22 allows cellular migration to the insert 16. The entire top surface 40 of the insert 16 is exposed to the articular environment of the affected joint, and a substantial portion of the bottom surface 42 of the insert 16 is exposed to the cancellous bone. The degree of communication between the area of removed damaged articular cartilage and the healthy cancellous or trabecular bone, is determined by the size, shape and placement of the system components and is selected to provide a desirable level of communication without unduly deleteriously affecting the strength of the delivery unit 14.

The delivery unit 14 is flexible and preferably resilient, so that it does not bend or deform unduly under expected pressures. It is preferably integrally molded. It is critical that the delivery unit 14 be made of a bio-absorbable material (e.g., without ceramics) such as those well known in the implant art. For example, it is preferably made of polyglycolic acid, polylactic acid or combinations thereof (e.g., copolymers and mixtures thereof).

Several delivery units 14 can be placed contiguously in an area of removed damaged articular cartilage such that a large portion of the removed area will be filled with the assemblies 12. In this case, the delivery units 14 are preferably regular polygons and interfitting in an abutting and contiguous relation. A circular delivery unit may be used where only one delivery unit is employed or where only partial coverage of the removed area is desired. Indeed, as set forth hereinbelow in detail, special circular delivery units may be particularly desirable in tiling a work area.

The insert 16 is made substantially of porous material in the form of a matrix or sponge, preferably defining at least 95% voids by volume, so that it can serve as a biological scaffold for an invasion of cells to regenerate the articular cartilage. It typically has the felt-like feel of a non-woven fabric. The insert 16 may be manually bendable or flexible so that one can push, press or snap the same onto the delivery unit 14. It is critical that the insert 16 consists substantially (typically at least 95% of the inorganic components by weight) of a bio-absorbable material selected from the group consisting of hyaluronic acid (e.g. as a fiber matrix), polyglycolic acid (e.g., as fiber matrix), collagen, including type I collagen (e.g., as a sponge matrix), polylactic acid (e.g. as a fiber matrix), fibrin clot (which can be filled and molded into the delivery unit), collagen gel (which can be overlayed into a polyglycolic acid matrix), polydioxane, polyester, alginate or combinations thereof. The polylactic acid, and to a lesser degree the hyaluronic acid, polyglycolic acid, and alginate, contribute to the hardness and longevity (i.e., life in situ after implantation) of the insert 16.

The insert may be annealed (i.e., heat-treated or cooked) to modify its crystallinity and thus its hardness and longevity.

In addition, in a preferred embodiment of the invention, the insert 16 can contain within the matrix "repair factors" such as growth factors and/or attachment factors and/or cell factors well known in the medical arts. For example, the insert 16 can contain, as growth factors, fibroblast growth factor (acidic or basic), transforming growth factor-beta (1, 2, 3 or one of the members of the supergene family of TGF-beta, such as bone morphogenic protein (BMP)), insulin, insulin-like growth factor 1 & 2 (IGF), platelet-derived growth factor or combinations thereof. The attachment factors which can be used in the insert include fibronectin, RGD polypeptide and combinations thereof. Typically, the repair factors total less than 1% by weight of the insert, but can range up to 10% depending on the factors' specific activities and release kinetics. The repair factors may be chemically combined with the basic implant composition (e.g., during polymerization thereof) or may be added to an already formed basic implant composition. in the former case, additional repair factor will typically become available as the basic implant composition biodegrades. As the cell factors, the insert may also include at least partially non-bio-absorbable cartilage or cartilage progenitor cells (such as isolated periosteal cells) which may be cultured in the insert material or grown ex vivo and then overlaid, instilled or injected at the time of surgery into the insert material. Other cell types, such as mesenchymal stem cells, tissue (e.g., small intestine submucosa), chondrocytes, cells containing genes specific for cartilage formation and maintenance of phenotype (e.g., collagen type II, aggrecon, hedgehog genes, etc.) and genetically engineered cells may also be a part of or added to the insert material. Indeed, bio-absorbable or essentially bio-absorbable pieces of ex vivo cartilage may be employed in the insert.

After surgical removal of the damaged or destroyed articular cartilage, the elongate member 26 of delivery unit 14 (extending downwardly from the support arms 28) is placed into the cancellous bone through the subchondral bone plate located below the damaged articular cartilage area so that the support arms 28 are adjacent the subchondral bone plate. The elongate member 26 has a blunt bevelled bottom so that it can be placed easily into the cancellous bone, which is a soft region of the bone. The bottom of the elongate member 26 is preferably blunt so that the bottom does not break as the elongate member 26 is being placed inside the cancellous bone. When the elongate member 26 is placed into the soft cancellous bone, the cancellous bone is displaced by, and then reforms around the elongate member 26. In this manner, the elongate member 26, and thereby the entire cartilage repair system 10, is held in place.

When the delivery unit 14 is placed in the bone, the insert 16, and typically the top surface of the elongate member 26, is coplanar with undamaged articular cartilage. The support arms 28 and the insert 16 are not placed inside the bone, but rather remain exposed to the surrounding articular cartilage in the space between the bone and the insert. The top surface 40 of the insert 16 is exposed to the joint space environment. The top portion of the exterior surface of the delivery unit 14 laterally abuts either the top portion of the exterior surface of an adjacent delivery unit 14 or undamaged articular cartilage (when placed adjacent a peripheral portion of an area of removed cartilage). The bottom portion of the exterior surface of the elongate member 26 of the delivery unit 14 rests on and laterally abuts the subchondral bone plate.

When the cartilage repair system of the invention is placed in an area of removed damaged articular cartilage, through the subchondral bone plate into the cancellous bone, communication is established between the healthy cancellous bone and the damaged articular cartilage area via a chondrogenic growth-supporting matrix—namely, the insert 16. This permits vascular invasion and cellular migration, which results in regeneration of the articular cartilage. The regenerated articular cartilage is functionally similar to undamaged articular cartilage. The cartilage repair system of the invention is bio-absorbed over time and therefore need not be surgically removed during or after cartilage regeneration. The absorption rate is formula controlled and can range from 6–12 weeks to one year or more depending on its site-specific application.

As the basic bio-absorbable composition of the insert 16 degrades or hydrolyzes over time, any repair factors contained therein are progressively released into the site, thus further promoting cellular regeneration. Cellular regeneration occurs throughout the insert.

Figure 6:
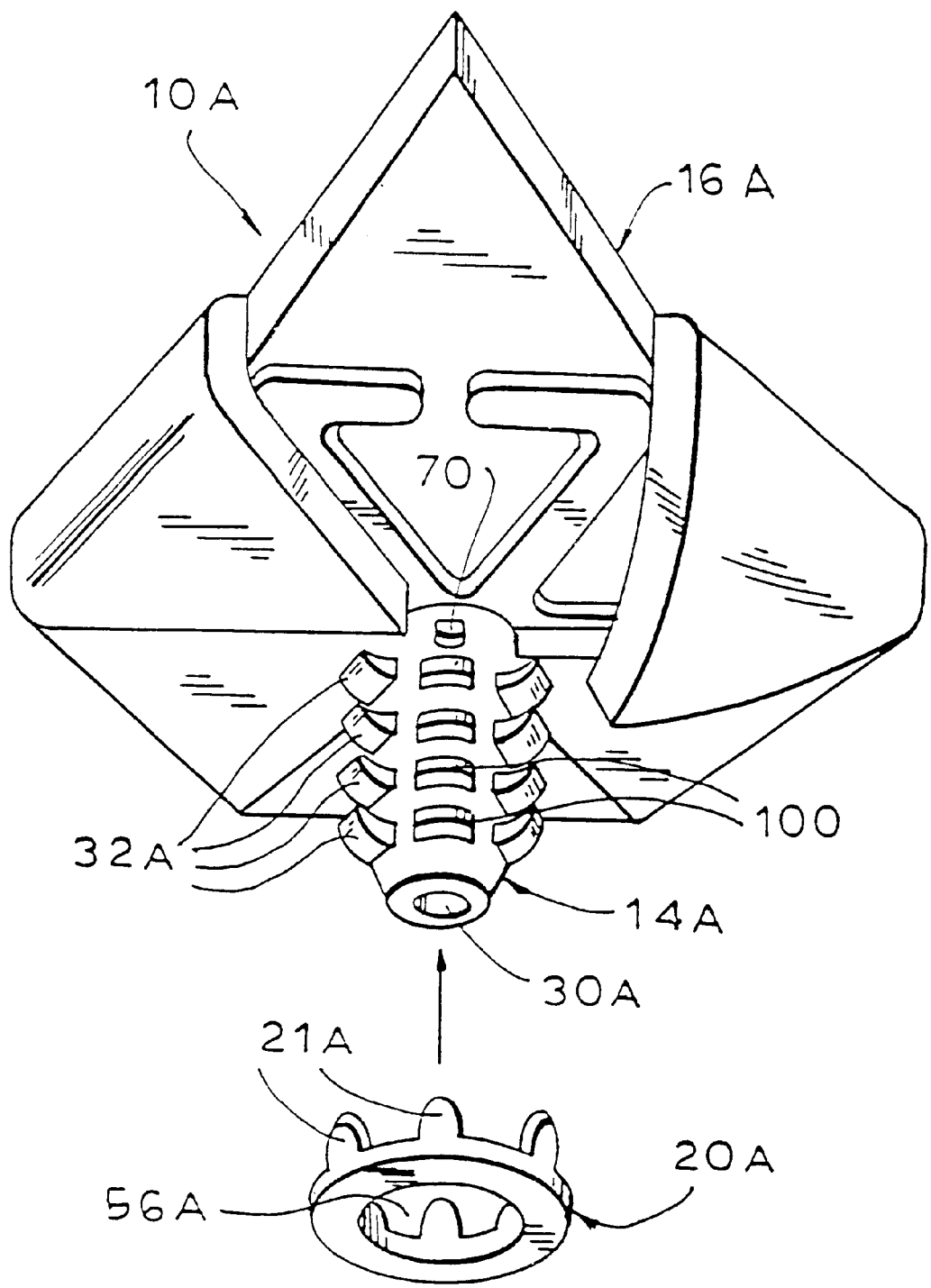
FIG. 6 is a partially exploded isometric view of a second embodiment of the present invention.

Referring now to FIG. 6 in particular, therein illustrated is a second embodiment 10A of the system of the present invention. In this embodiment 10A the functions of the insert 16 and porous film 22 are performed by a single flexible element 16A. The element 16A is illustrated in FIG. 6 in an intermediate stage—that is, as being partly wrapped around the delivery unit 14A. The securing device 20A is insertable onto the elongate member 26 of the delivery unit 14A so that the element 16A is held in place by upwardly projecting locking barbs 21A.

The delivery unit 14A differs from the delivery unit 14 in that the elongate member 26A of the delivery unit 14A is circular in cross section, defines a longitudinally extending plurality of longitudinally spaced windows 100 therein leading to bore 30A, and has a longitudinally-extending series of circumferentially spaced, radially-extending steps 32A (and no counterpart of flange 70). The windows 100 promote communication between the cancellous bone and the insert 16A, as do the vertical spaces between the steps 32A.

If desired, the retainer 20A may have a slightly different configuration than retainer 20, with the retainer 20A lacking barbs or projections upstanding from the base thereof.

While the first embodiment 10 is shown and described herein as having the porous film 22 and insert 16 separate and distinct, the second embodiment 10A is shown and described herein as having the single flexible element or wrap 16A combining the insert and the porous film functions. Clearly the choice between a pair of elements 16, 22 or a single flexible element or wrap 16A for any given delivery unit 14 and retainer 20 is a matter of choice to be made depending upon the particular application intended.

Referring now to FIGS. 7 and 8 in particular, therein illustrated is a third embodiment 10B of the present invention. The third embodiment 10B includes a perforated and preferably porous film 22B, a delivery unit 14B (including an elongate member 26B and three radial arms 28B) and a pair of inserts 16B (perforated therethrough by several relatively small holes). The inserts 16B form a sandwich with the support arms 28B when the top insert 16B is disposed above the radial arms 28B and the bottom insert 16B is disposed under the radial arms 28B. The support arms 28B are optionally fewer in number than in support 28 and preferably define triangles open in the center thereof. The elongate member 26B is provided with a longitudinally extending series of circumferential steps 32B. While the porous film 22B, upper insert 16B, and delivery unit 14B define central apertures 30B, the bottom insert 16B defines a somewhat larger aperture 30B enabling it to be fit over the elongate member 26B.

Needling of the porous film 22B and the inserts 16B after assembly may suffice to maintain the assembly elements together, thus avoiding the need for a retainer 20B. Preferably the needling would occur only in areas not occupied by the material of delivery unit 14B.

Referring now to FIGS. 9 and 10 in particular, therein illustrated is a fourth embodiment 10C of the present invention, which dispenses entirely with the need for either a porous film or wrap 22 or a retainer 20. In this embodiment, the delivery unit has a plurality of radially-extending support arms 28C. Each radial arms 28C includes a proximal transverse member 110 and a distal transverse member 114. The proximal transverse member 110 has an enlarged end 112 at each end, while the distal transverse member 114 has an enlarged end 116 at each end. The enlarged ends 112, 116 are beveled to facilitate their passage through the inserts 16C in one direction, while blocking passage therethrough in the opposite direction. During assembly of the system 10C, the elongate member 26C is passed downwardly through the bottom insert 16C so that the enlarged ends 112, 116 of the transverse members 110, 114 pass therethrough and act to hold the lower insert 16C in position. Then the upper insert 16C is brought down on the radial arms 28C with the enlarged upper ends of the proximal transverse members 110 extending into the upper insert 16C and the upper enlarged ends 116 of the distal transverse members 114 extending through the upper insert 16C, thereby to retain the upper insert 16C on the radial arms 28C. To further secure the two inserts 16C and the radial arms 28C together, heat may be applied to at least partially melt the radial arms 28C. Thus, upon cooling, both inserts 16C and the radial arms 28C bond together. Typically either the transverse members 110, 114 are barbed and a mechanical lock is achieved or the transverse members 110, 114 are not barbed and a melt-based lock is achieved.

Still referring now to FIGS. 9 and 10, the fourth embodiment 10C further illustrates a removable delivery unit 14C having a spreadable and retractable elongate member 26C. Thus, the elongated member 26C is divided or partially split into two components 117. The two components 117 are preferably biased towards one another to facilitate introduction of the elongate member 26C into the operative site. Thereafter, however, an element 118 (preferably having a forward tip of wedge shaped design), is inserted from above into the bore 30C of the elongate member 26C via the inserts 16C. The element 118 may be externally threaded (in which case the bore 30C of the elongated member 26C is internally threaded) or it may simply be a nail. In either case, after insertion of the unit 10C into the surgical site, the driving of the element 118 through the upper insert 16C and into the bore 30C of the elongated member 26C spreads the two components 117 apart, thereby improving the fixation of the unit 10C within the cancellous bone. Should it ever prove desirable, the element 118 may be removed (either by being counter-rotated in the case of a threaded engagement or simply pulled up from a non-threaded engagement), thereby allowing the two components 117 to approach one another and facilitate removal of the entire insert 10C from the operative site.

Figure 12A:
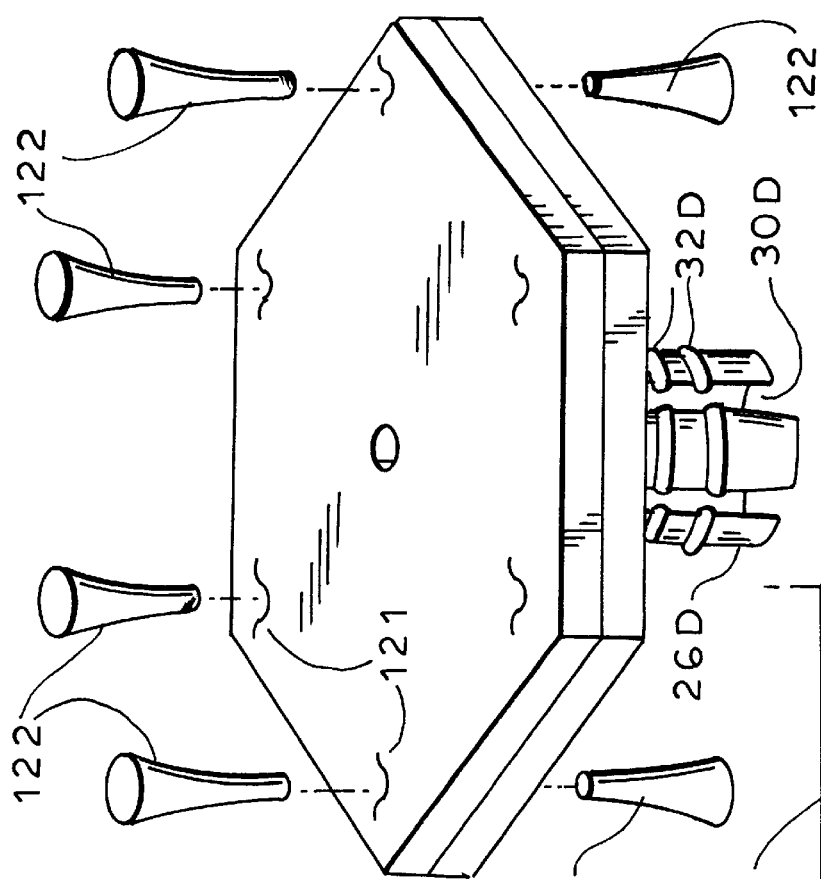
FIG. 12A is a partially exploded isometric view of the fifth embodiment undergoing sonic welding.
Figure 12B:
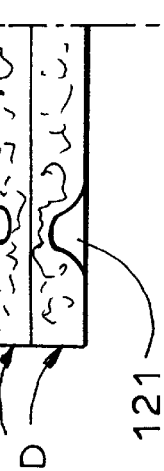
FIG. 12B is a fragmentary sectional view of the fifth embodiment.
Figure 11:
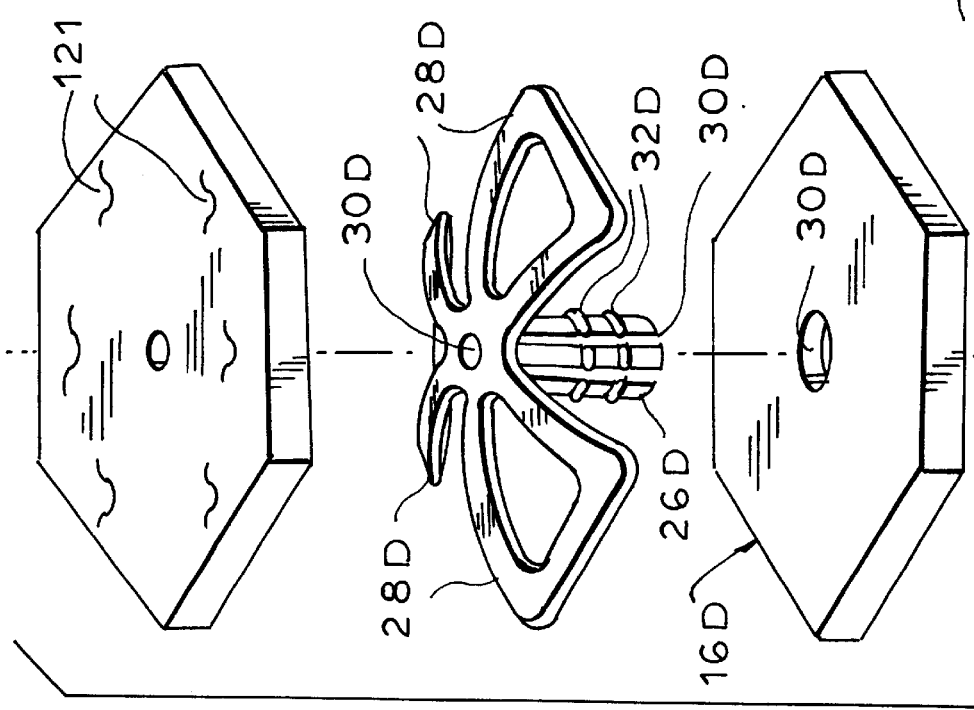
FIG. 11 is an exploded isometric view of a fifth embodiment.

Referring now to FIGS. 11–12B, therein illustrated is a fifth embodiment 10D of the present invention. The radial support arms 28D are triangular in configuration, with a central opening in each, and are sandwiched by an upper insert 16D and a lower insert 16D. However, instead of being secured to the support arms 28D of the delivery unit 14D by barbed stakes and/or heat welding (as in the fourth embodiment 10C), the upper and lower inserts 16D are maintained in place on the radial support arms 28D because they are sonically welded together and optionally to the arms 28D. To facilitate this, the upper surface of the upper insert 16D and the lower surface of the lower insert 16D are provided with circumferentially spaced indentations 121 which will be positioned between a pair of sonic welders 122 during the sonic welding process. (The indentations 121 in the lower insert 16D are visible in FIG. 12B.) The main weld is located between the indentations 121. As sonic welding is a well known procedure, further details thereof are not deemed necessary therein.

As in the previous embodiments where the bottom insert 16 has to pass upwardly over the elongated member 26 of the delivery unit 14, the small aperture 30D of the lower insert 16D is enlarged in dimension to be received over the elongate member 26D.

Referring now to FIGS. 13A and 13B in particular, therein illustrated is a sixth embodiment 10E of the present invention. In the embodiment 10E, at the time of implantation, a delivery unit 14E is partially inserted through a single insert 16E disposed over a prepared cancellous bone site 148 such that the arms 28E extend upwardly and outwardly to fix the insert 16E to the prepared bone site 148. In the preferred embodiment illustrated, arms 28E hold insert 16E' in place directly over the delivery unit 14E. Accordingly, the insert portions 16E and 16E' cooperatively define a substantially continuous insert surface when the assembly is inserted.

Figure 15:
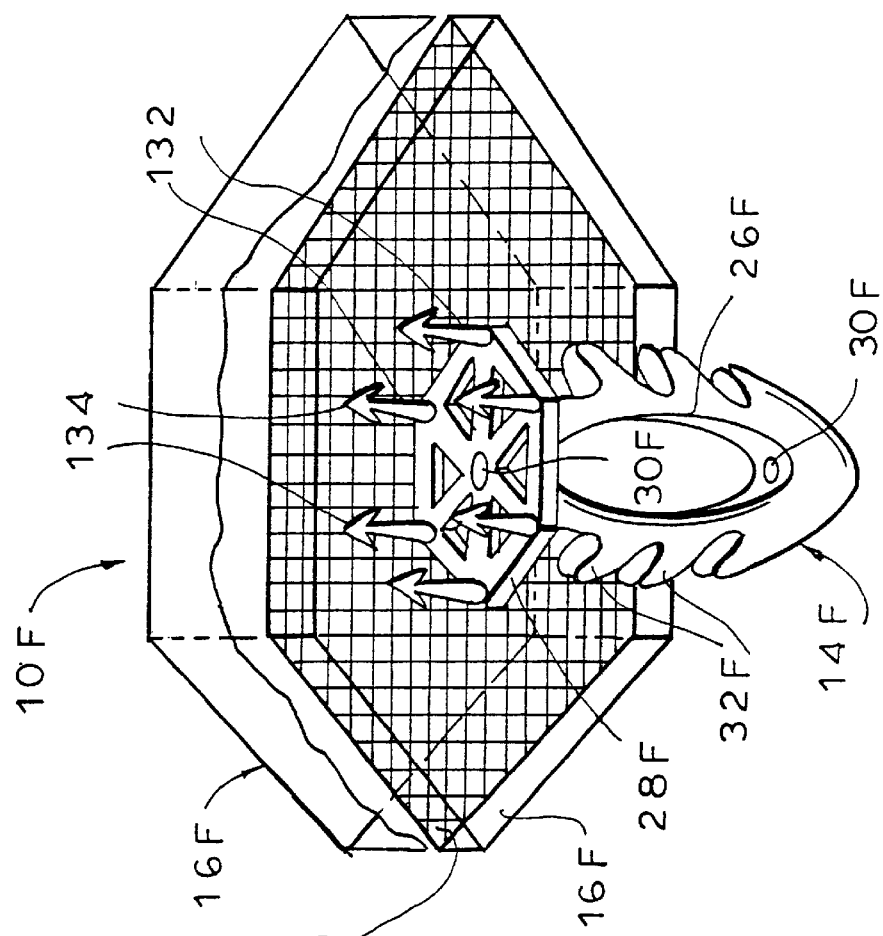
FIG. 15 is an isometric view of the seventh embodiment.
Figure 14:
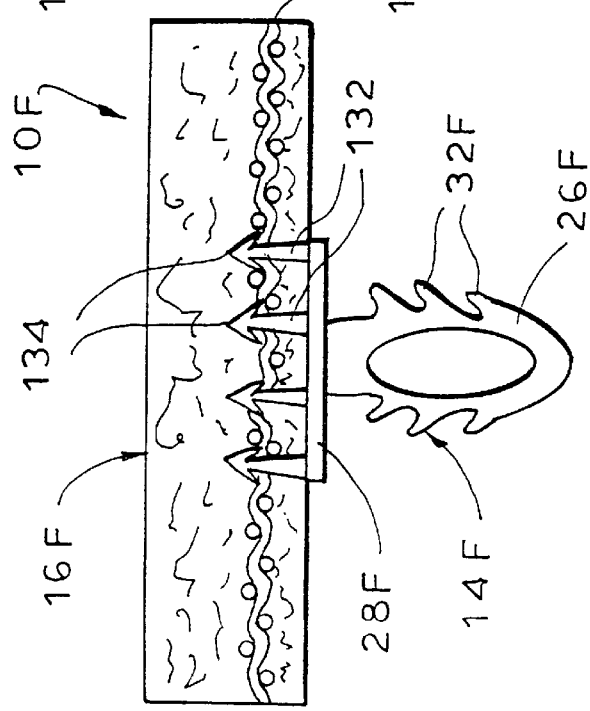
FIG. 14 is a side elevational view, partially in cross-section, of a seventh embodiment.

Referring now to FIGS. 14 and 15 in particular, therein illustrated is a seventh embodiment 10F of the present invention. The insert 16F includes a relatively rigid, screen-like, bio-absorbable middle layer 130 of ceramic-free, bio-absorbable fabric, and the top of the delivery unit 14F defines a plurality of upstanding lugs 132 having spiked tips 134 of sufficient length to penetrate the fabric layer 130 and thereby hold the insert 16F in place on the delivery unit 14F. For example, there may be six circumferentially spaced barbed lugs 132 projecting upwardly from the top of the delivery unit 14F. Preferably the middle layer 130 is surrounded by upper and lower layers of the insert 16F.

Referring now to FIGS. 16 and 17 in particular, therein illustrated is an eighth embodiment 10G of the present invention. The insert 16G includes an upper layer and a lower layer. The delivery unit 14G includes a pair of radially extending arms 28G terminating in hooks 136. The hooks 136 extend both upwardly into the upper layer and downwardly into the lower layer of the insert 16G. To assemble the unit 10G, the radial arms 28G are interposed between the upper and lower layers of the insert 16G, and the two elements 28G, 16G are then rotated slightly relative to each other in order to cause the hooks 136 to bite into and join the upper and lower insert layers. Preferably the upper and lower layers of insert 16G contain a plurality of cuts or recesses 138 (equal in number to the plurality of radial arms 28G) which enable the upper and lower layers of the insert 16G to be disposed snugly on the radially-extending arms 28G such that the hooks 136 grab both the top and bottom layers after the delivery unit 14G and the insert 16G are rotated relative to one another.

Referring now to FIGS. 18–20 in particular, therein illustrated is a ninth embodiment 10H of the present invention. The embodiment 10H uses a single layer insert 16H and a delivery unit 14H having at the top thereof a plurality of upwardly and outwardly extending arms 28H (four being shown). The insert 16H is centrally cut or slit appropriately at 138 to receive the arms 28H therein when the tips thereof are externally maintained relatively close together as illustrated in FIG. 18. However, when the tips are released, the downwardly and outwardly biased radial arms 28H flatten somewhat and extend further radially outwardly than before, now extending out of the cut or slit 138 and into the actual material of the insert 16H. In this embodiment it is important that the radially-extending arms 28H be relatively strongly resilient so that they enter the insert 16H about the cuts or slits 138 as the delivery unit 14H and the insert 16H are pressed together and the external force on the arms 28H is released.

Figures 21, 22, 23:
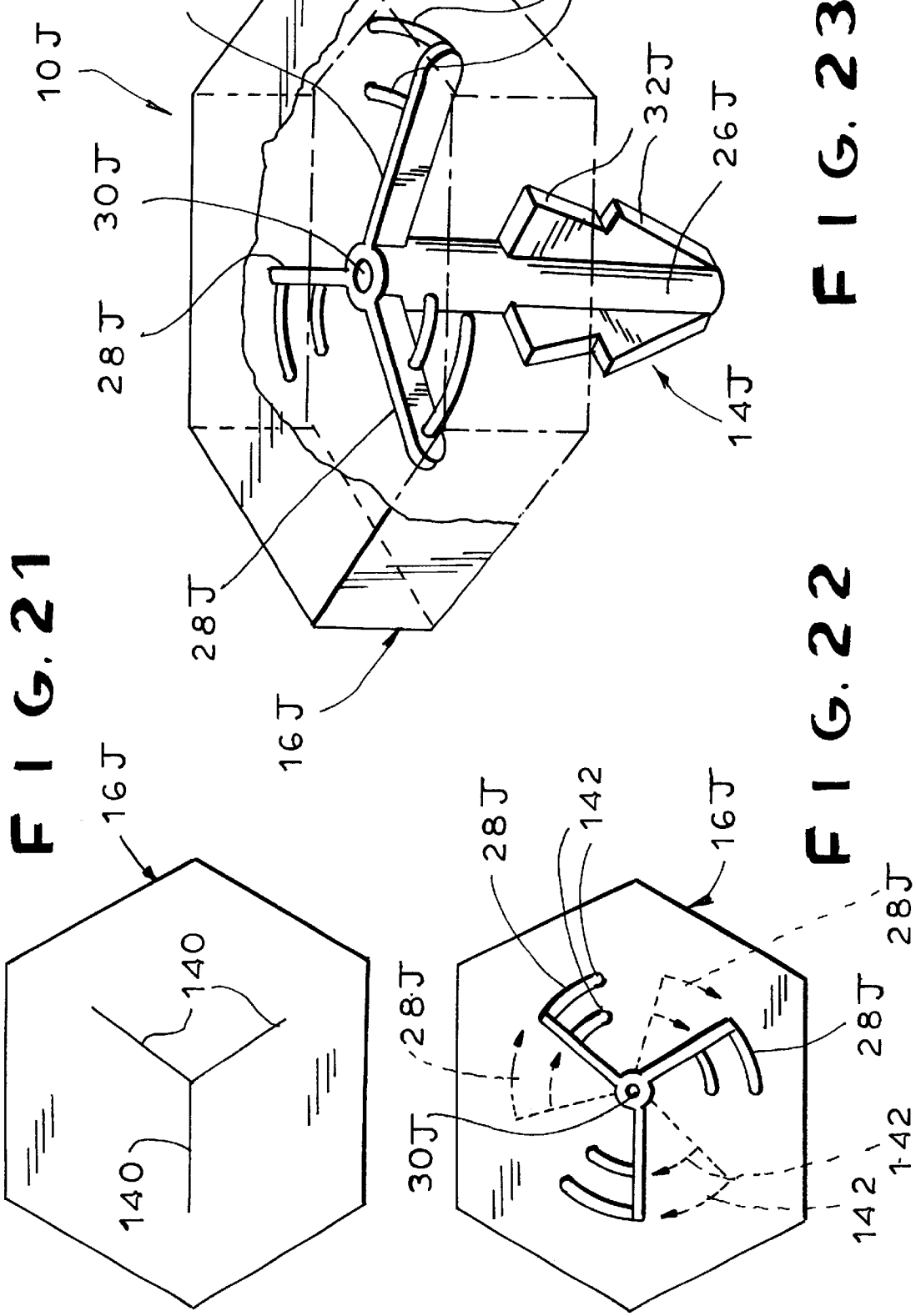
FIG. 21 is a bottom plan view of an insert of the tenth embodiment.
FIG. 22 is a top plan view of the tenth embodiment, with upper layers being removed to reveal details of internal construction and with the delivery unit shown in its original position in dotted line and in its final position in solid line.
FIG. 23 is an isometric assembly view of the tenth embodiment.
Figure 24:
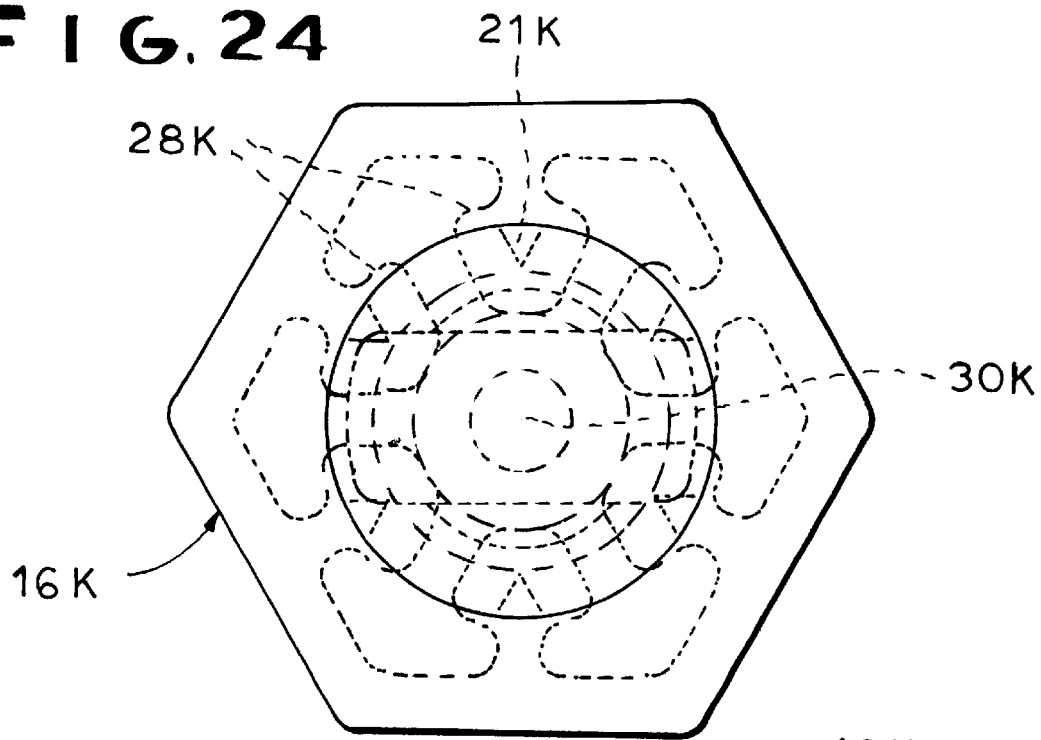
FIG. 24 is a top plan view of the eleventh embodiment.
Figure 25:
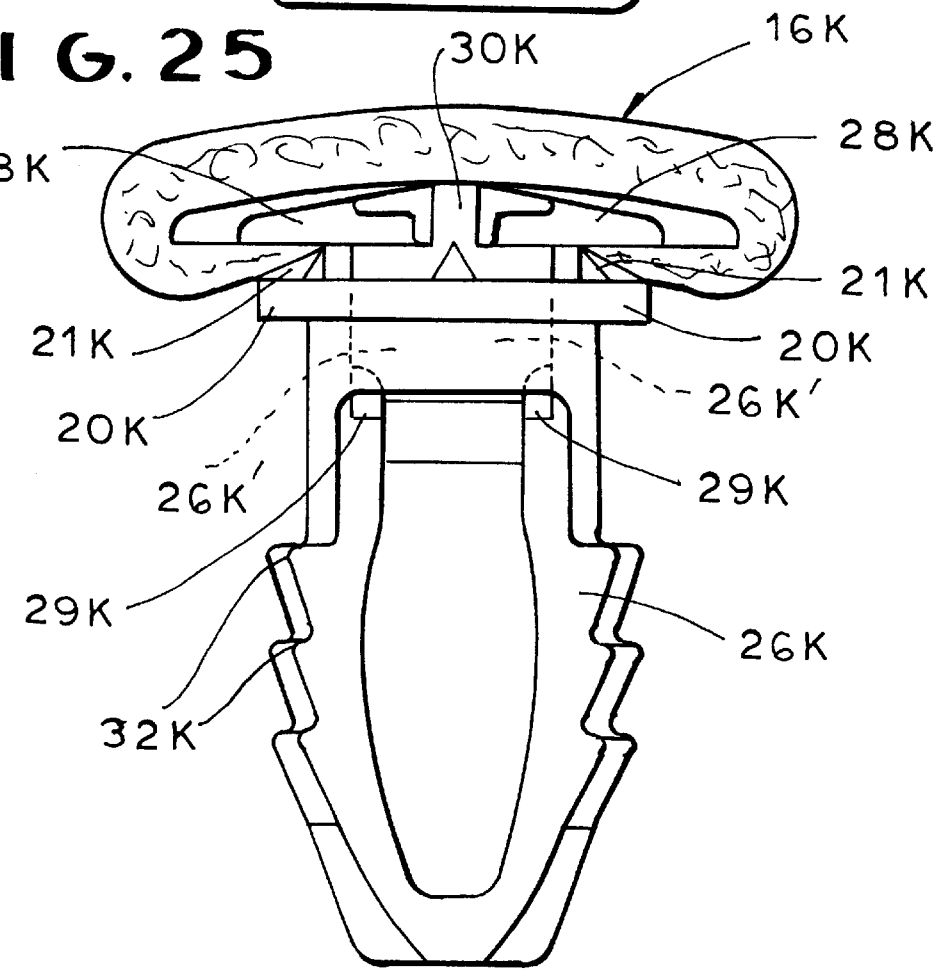
FIG. 25 is a side elevational view, partially in cross section, of the eleventh embodiment.

Referring now to FIGS. 21–23, therein illustrated is a tenth embodiment 10J of the present invention. The embodiment 10J uses a one-piece insert 16J provided with cuts or slits through at least the bottom portion thereof. The delivery unit 14J has at the top thereof a plurality of radially extending arms 28J, each defining a transversely-extending pair of fingers 142 adapted to fit into cuts 140 of insert 16J. Thus, when the insert 16J and the delivery unit 14J are interposed and then rotated relative to one another, the fingers 142 bite into the insert 16J in order to maintain the insert 16J on the delivery unit 14J, as illustrated in FIG. 22 (where the phantom line representation of the delivery unit 14J indicates the initial position of the arms 28J and the solid line representation indicates the final position of the arms 28J).

The arms 28 and the elongate member 26 may be of integral, unitary, one-piece construction formed in a single operation, or they may be separately formed and subsequently joined together to define a delivery unit 14.

In reviewing the several embodiments described and illustrated, it will be appreciated that retainer rings 20, 20A and 20B are not required for the fourth embodiment 10C through the tenth embodiment 10J as these embodiments 10C–10J lack the film (whether porous or perforated) 22, 16A, 22B of the first, second and third embodiments 10, 10A, 10B. Functionally the various retainer rings 20, 20A and 20B of the first, second and third embodiments 10, 10A, 10B, respectively, are with minor modifications interchangeable.

It will further be appreciated that inserts 16 of the first embodiment, 16A of the second embodiment, 16E of the sixth embodiment, 16F of the seventh embodiment, 16H of the ninth embodiment, and 16J of the tenth embodiment are of unitary design rather than being composed of two separate insert layers (although insert 16F requires the presence of a fabric layer 130). By way of contrast, inserts 16B of the third embodiment, 16C of the fourth embodiment, 16D of the fifth embodiment, and 16G of the eight embodiment, require a two-part insert with a top insert layer initially separated from a bottom insert layer.

Of course, the porous film may be formed of and as a part of the insert, as illustrated in insert 16A of the second embodiment.

It will also be understood that while the radial arms may extend outwardly without forming a closed geometrical figure therebetween (as in arms 28 of the first embodiment, 28A of the second embodiment, 28C of the fourth embodiment, 28E of the sixth embodiment, 28G of the eighth embodiment, 28H of the ninth embodiment, and 28J of the tenth embodiment), in some embodiments the radial arms preferably define a geometric pattern—e.g., a triangle which is open in the interior thereof (as in arms 28B of the third embodiment, 28D of the fifth embodiment, and 28F of the seventh embodiment). The open spaces in the closed figures facilitate communication between the insert thereabove and the cancellous bone therebelow. Where a pair of adjacent arms define a closed geometrical figure, the arms are more strongly resilient and better able to withstand pressures thereon without deflecting or breaking.

While the radial arms may simply be barbed in a horizontal plane (as in arms 28 of the first embodiment, 28A of the second embodiment, 28B of the third embodiment, and to some degree 28E of the sixth embodiment), the radial arms may have barbs in one or both directions in a vertical plane (as in radial arms 28C of the fourth embodiment, 28F of the seventh embodiment, 28G of the eighth embodiment, and to some degree 28E of the sixth embodiment).

The elongate member or bottom portions of the delivery units are preferably open at the sides thereof or possessed of windows 100 on the sides thereof (for communication with the internal bore), except for the elongate members 26E of the sixth embodiment and 26J of the tenth embodiment. Where the elongate member is devoid of sides, any retainer means therefor preferably defines a somewhat elongated central aperture coaxial with the aperture of the internal bore, as in retainer means 20 of the first embodiment. But where the elongate member is essentially circular in cross section, as in elongate members 26A of the second embodiment and 26B of the third embodiment, a retainer means 20A, 20B, respectively, which defines a circular opening 56A, 56B, is preferably employed. Alternatively, an equivalent structure may be employed wherein the insert is barbed (to grip into the retainer means) instead of the retainer means being barbed (e.g., having barbs 21A).

Important considerations in the selection of one embodiment relative to another include the ease with which a surgeon or other operating room personnel may secure together the unit and the insert (including the number of different components which must be juggled at once in order to assemble the repair system), the relative costs, the ability of the elongate members of the delivery units to provide exposure of the insert to adjacent inserts, healthy cartilage and cancellous bone, ease of manufacture of the components, etc.

The preceding embodiments 10–10J are directed to an assembly of at least a delivery unit and a matrix or insert, wherein the delivery unit adjacent to the top thereof provides a support for the matrix or insert and adjacent to the bottom thereof provides means for mounting the delivery unit in cancellous bone. In yet another embodiment of the present invention, the delivery unit may be itself a sub-assembly of two separately formed components—namely, means for supporting the matrix or insert and means for anchoring the delivery unit in cancellous bone.

Referring now to FIGS. 24–28 in particular, therein illustrated is an eleventh embodiment 10K of the present invention. Here the radial support arms 28K and related support means 26K' for supporting the insert 16K are formed separately from the retaining means 26K for fixation to cancellous bone and its related means (outwardly extending steps 32K and barbs 21K), as illustrated in the exploded isometric view of FIG. 26. It will be appreciated that the insert 16K is partially cut away in FIG. 24 and not shown at all in FIGS. 26–28. The support arms 28K and support means 26K' are secured to the retaining means 26K, extending steps 32K, barbs 21K by a snap-in fastening system or other conventional means. In the snap-in configuration the support system defines adjacent the bottom thereof resilient outwardly extending projections 29K adapted to lock the support system in place on the fixation system by an interference fit with outwardly extending shoulders 33K, which extend above projections 29K when the two systems are assembled to form a delivery unit, as illustrated in FIGS. 27 and 28.

A major advantage of this construction (the eleventh embodiment 10K) is that a preferred specific design of the radial arms of any of the embodiments (or other means for supporting the insert) may be employed with a preferred specific design of the means for retaining the delivery unit in cancellous bone of any of the embodiments (or other means for anchoring the insert support means in cancellous bone), so that an optimum combination of these two designs for a particular injury in a particular patient may be selected by the surgeon in the operating room after the injury is visualized. For example, the arms of 28K may be of differing lengths or geometries to best fit the defects to be regenerated.

The bio-absorbable cartilage repair system embodiments 10–10K described above have been described in the context of a single assembly consisting of a delivery unit and an insert or matrix. However, as will be appreciated by those skilled in the surgical arts, frequently the area of damaged or destroyed articular cartilage is so great as to require the use of more than a single assembly. In this instance, considerable skill on the part of the surgeon is required in order to place the two assemblies, and in particular the two delivery units, as close to one another as possible so as to promote cartilage regeneration over the entire area of damaged or destroyed articular cartilage that has been removed. Alternatively, the requisite skill of the surgeon may be rendered unnecessary through the use of surgical devices (e.g., spacers) which ensure appropriate placement of the delivery units in the desired side-by-side relationship. Such surgical devices are not part of the assemblies themselves, must be removed after the assemblies have been properly positioned in the patient, and, at least to some degree, interfere with visualization of the work area by the surgeon. Accordingly, the present invention also encompasses bio-absorbable cartilage repair systems which in effect utilize a plurality of delivery units and ensure that the delivery units will be appropriately positioned in the work area, like tiles, with a minimum of effort by the surgeon.

In order to effect this result, two distinct novel approaches are utilized.

Figure 29:
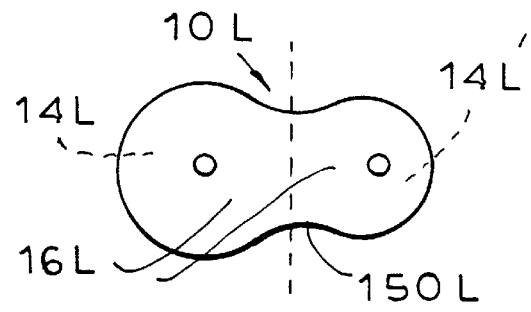
FIGS. 29 and 30 are top plan and side elevational views, respectively, of the twelfth or duplex embodiment in an unfolded orientation.
Figure 30:
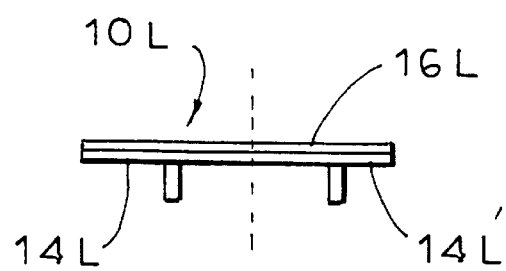

Referring now to FIGS. 29–32, therein illustrated is a twelfth embodiment 10L of the present invention in the form of a duplex assembly. For the purposes of illustrating the principle of this duplex embodiment, it is only necessary to recognize that there are at least two delivery units 14L, 14L' and a single insert 16L. The insert 16L extends over both of the delivery units 14L and 14L', as best seen in FIG. 30, and is preferably "8" shaped so as to provide full coverage of each delivery unit 14L, 14L' and a minimum width conjoining or juncture area 150L therebetween. For example, two delivery units 14L, 14L' having diameters of about 7–9 mm may be connected by an insert or matrix 16L defining a juncture or conjoining area 150L having a width of about 4 mm.

Figure 31:
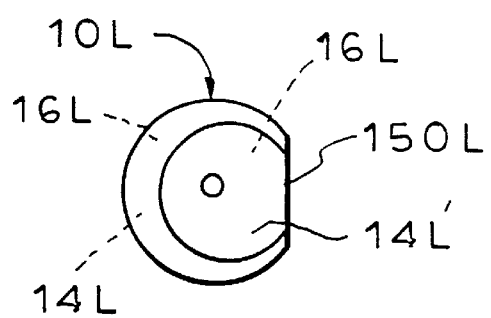
FIGS. 31 and 32 are top plan and side elevational views, respectively, of the twelfth embodiment in a folded orientation.
Figure 32:
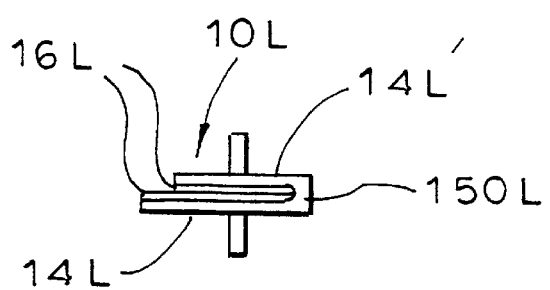

The duplex assembly 10L can be folded at the conjoining area 150L through an angle of approximately 180° so that the two delivery units 14L, 14L' are approximately on a common longitudinal axis, although pointed in opposite directions. As illustrated in FIGS. 31–32, the duplex assembly 10L, may be positioned in the patient in its folded state (for example, through a tubular applicator) and then, as illustrated in FIGS. 29–30, unfolded in the work area so that the delivery units 14L, 14L' thereof are closely adjacent and preferably in a side-by-side contiguous relationship. Once one of the delivery units 14L, 14L' of the duplex assembly 10L has been properly positioned in the work area, appropriate positioning of the other delivery unit 14L', 14L is automatic with unfolding of the duplex assembly 10L.

Figure 33:
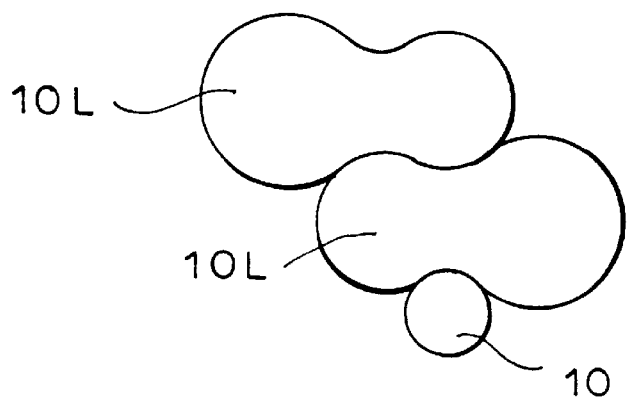
FIG. 33 is a top plan view of two contiguous twelfth embodiments and a non-duplex embodiment.
Figure 34:
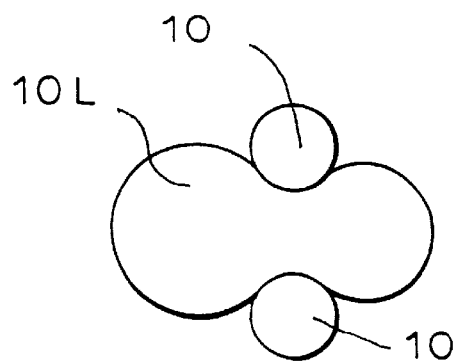
FIG. 34 is a top plan view of a single twelfth embodiment contiguous to two non-duplex embodiments, one on either side.
Figure 44:
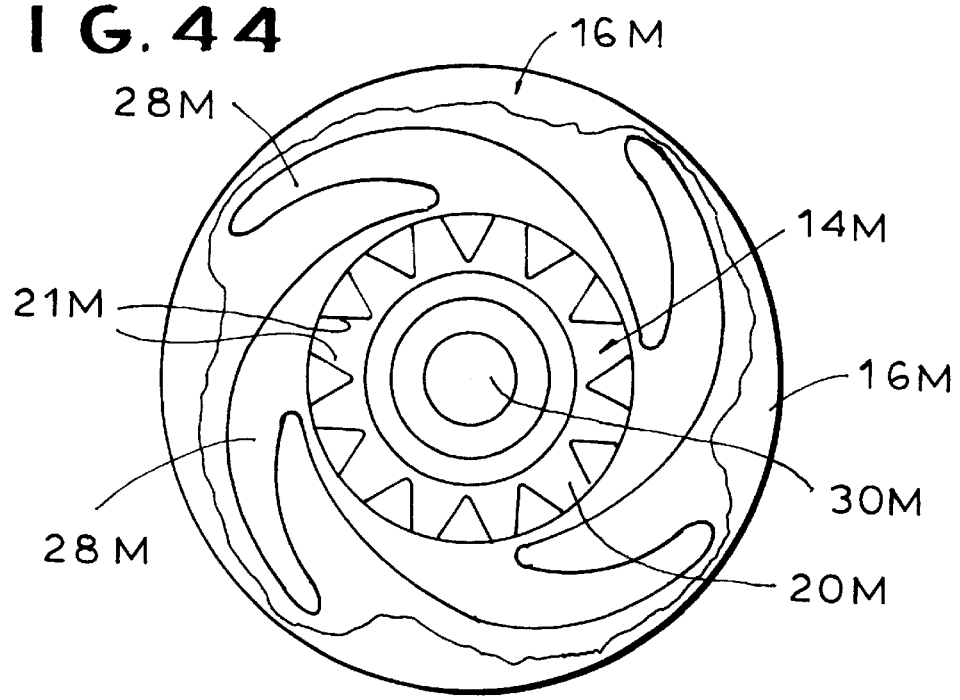
FIG. 44 is a side elevational view, partially in section, of a variant the thirteenth embodiment.

As illustrated in FIG. 33, two or more duplex assemblies 10L may be disposed in staggered contiguous relationship, if desired. As illustrated in FIGS. 33 and 34, a duplex assembly 10L may be in a contiguous relationship with a non-duplex assembly 10.

It will be appreciated that while the description above relates only to the placement of two delivery units 14L, 14L' in a contiguous side-by-side relationship, additional assemblies (whether of the same or different types) may be placed in contiguous relationship thereto in order to effect a complete tiling of the damaged articular cartilage area to be regenerated.

Referring now to FIGS. 35–36, therein illustrated is a thirteenth or compressible embodiment 10M of the present invention having a delivery unit 14M wherein the flexible, radially extending support arms 28M are of a spiral or helical design and resiliently compressible. In two dimensional terms, each support arm 28M describes a curve on a plane that winds around a fixed center point at a continuously increasing distance from the point; in three-dimensional terms, each support arm 28M describes a three-dimensional curve that lies on a cone extending through a longitudinal axis (e.g., the delivery unit axis) so that its angle to a plane perpendicular to the longitudinal axis is constant. For the purpose of illustrating the principle of this compressible embodiment 10M with spiral or helical support arms 28M, it is only necessary to recognize that at least one support arm 28M is biased outwardly at its free end (typically due to the resiliency of the support arm material) but resiliently displaceable inwardly under manual pressure.

Preferably, as illustrated, there are four support arms 28M so that each support arm extends over only a fourth of the circumference of the delivery unit 14M, although a greater or lesser number of support arms 28M may be used. As illustrated, the four support arms 28M have an octagonal matrix or insert 16M wrapped thereabout to provide an overall hexagonal appearance to the top of the assembly 10M, although a matrix or insert 16M having a greater or lesser number of sides may be used.

While the assemblies of FIGS. 1–36 have been described hereinabove as preferably being polygonal or at least partially polygonal at the level of the insert so as to enable adjacent and even contiguous placement of a plurality of assemblies, clearly almost any of such assemblies may instead be substantially circular. For example, in a variant of the thirteenth embodiment 10M illustrated in FIGS. 37–42 the peripheral configuration is circular. A circular configuration for the upper portion of the assembly facilitates the procedure for creating the cavity into which the assembly will be placed. A circular drill or the like may be used to create the circular cavity rather than the chisel required to form the polygonal cavity.

After one such circular assembly 10M in compacted configuration (FIG. 37) has been properly positioned in the work area, a second such circular assembly 10M' in compacted configuration may be placed in the work area with the second assembly 10M' being closely adjacent or contiguous to the first assembly 10M, such that portions of the outer peripheries of the later expanded first and second assemblies 10M, 10M' attempt to occupy the same space, with the inevitable result that there is necessarily an inward flexing of at least one adjacent radial arm 28M of one expanded assembly 10M, at least one adjacent radial arm 28M' of the other expanded assembly 10M', or the adjacent radial arms 28M, 28M' of both expanded assemblies 10M, 10M' (FIG. 40). The helical or spiral design of the radial arms of the thirteenth embodiment 10M enables an easy adjustment of the effective diameter of the assembly, thereby to enable a plurality of such assemblies to be closely positioned within the work or tiling area.

If desired, as illustrated, additional assemblies 10M of this type may be added as necessary to fill the work or tiling area. Naturally, this type of assembly 10M may also be used in conjunction with the previously described assemblies, with the understanding that substantially all of the resilient compression of the support arms will occur in the assembly of this type.

When it is necessary to insert two such circular assemblies 10M, 10M' side by side, a problem arises because the peripheries of the two circular assemblies will contact only tangentially, thereby leaving a substantial area which will not directly receive the benefit of the assemblies. In order to overcome this tiling problem (which typically arises only when two or more circular assemblies 10M are to be placed in adjacent or contiguous positions), the support arms 28M of at least one such circular assembly and preferably the support arms 28M of both such circular assemblies, are flexible. Thus the peripheries of the circular assemblies 10M may be placed close together, and even in a somewhat overlapping relationship, because the overlapping peripheral portion of at least one circular assembly (and preferably both circular assemblies) is capable of deflecting (i.e., flexing vertically) to accommodate the overlapping peripheral portion of the other circular assembly. More particularly, at least one support arm 28M of the circular assembly is flexible or at least deflectable. The extent of the delectability or flexibility of the circular assembly may be controlled by the tightness of the porous film or wrap 22M about the support arms 28M, a looser wrap resulting in more deflectable support arms.

Installation of the thirteenth embodiment 10M, 10M' is facilitated by maintaining each assembly in a tightly compressed or compact state (as by keeping it within a removable hollow cylindrical tube 160) and installing as many adjacent assemblies in the compressed or compact state as necessary in the work area before removal of the hollow tube 160 from each assembly, with the resultant expansion of the support arms 28M, 28M'.

Alternatively, as illustrated in FIGS. 41–43, after assembly 10M in the compacted state (FIG. 41) is installed in the work area, the compressing means 160 is removed therefrom. Then an adjacent assembly 10M' in the compacted state (FIG. 42) is installed, with the surgeon (or the shape of the forward tip of compressing means 160) shoe horning or displacing any portion of a support arm 28M of the first assembly 10M from underneath the compressing means 160 of the adjacent assembly, after which compressing means 160 is then removed therefrom (FIG. 43). While the former insertion procedure (see FIGS. 39–40) is less demanding on the skills of the surgeon than the latter insertion procedure ( see FIGS. 41–43), it also requires a greater surgical exposure of the work area along with the obvious disadvantages thereof As will be appreciated by those skilled in the art, the compressibility of the delivery unit 14M minimizes the demand upon the skill of the surgeon for proper placement of the assemblies, as a group of compressed assemblies 10M which are somewhat misplaced can still adequately cover a work area without any interruption when allowed to expand. It will also be readily appreciated by those skilled in the art that the assembly 10M described above will have utility not only in the environment where two assemblies will be closely positioned, but even in the environment of a single assembly. For example, it may be desirable to maintain an assembly 10M in a compressed form during insertion into the patient, with the assembly then being allowed to expand.

While the preceding embodiments are directed to an assembly of at least a delivery unit and a matrix, the product may also be made as a single, unitary and integral product. To accomplish this, the intended product is first visually modeled in three dimensions on a computer as a computer aided design (CAD) file or, alternatively, data available from laser, x-ray, CAT or MRI scans can be imported into the CAD system and used in the design process. The resulting design is then used as the basis for engineering analysis and evaluation, using computer aided engineering (CAE) tools designed to work with CAD geometries. The final CAD data is then transferred to a machine which translates the CAD data into layer-by-layer information and then executes the motions to produce the final product. The fabrication of the intended product is accomplished with repeated cycles of spreading powder, selectively depositing binder on portions of the powder, and removal of unbound powder. The product is thus built vertically, layer-by-layer, preferably using photolithography techniques. The result is a product design that can be efficiently evolved to a final product form with the desired features and performance characteristics.

Accordingly, the term "assembly" is used in the specification and claims hereof to encompass both elements which are independently formed and then combined together, or elements which have been created in a single process, layer-by-layer, as disclosed above.

The term "bio-absorbable" is used in the specification and claims hereof to indicate a material which will be degraded or absorbed by the body such that regenerated articular cartilage thereabout is functionally similar to non-damaged articular cartilage.

The term "dimensionally stable" as applied to a material is used herein to indicate that the material does not appreciably expand in synovial joint fluid due to the absorption thereof. While there may be some slight dimensional expansion even under this definition, it is an insufficient amount of expansion to enable retention of the material by its environment (for example, the delivery unit in the case of the insert, and the adjacent healthy area of articular cartilage and subchondral cancellous bone in the case of the delivery unit).

While the assembly of the present invention has been described hereinabove as preferably having the insert 16 and the delivery unit 14 joined together prior to surgical implantation in a patient, the present invention also contemplates the initial surgical implantation of the delivery unit 14 (without the insert) followed by a subsequent addition of the insert 16 to the delivery unit 14 in situ. Embodiments of the present invention especially well suited for such in situ joining of an insert and a delivery unit are illustrated in FIGS. 14–15, 18–20 and 21–23.

Figure 45:
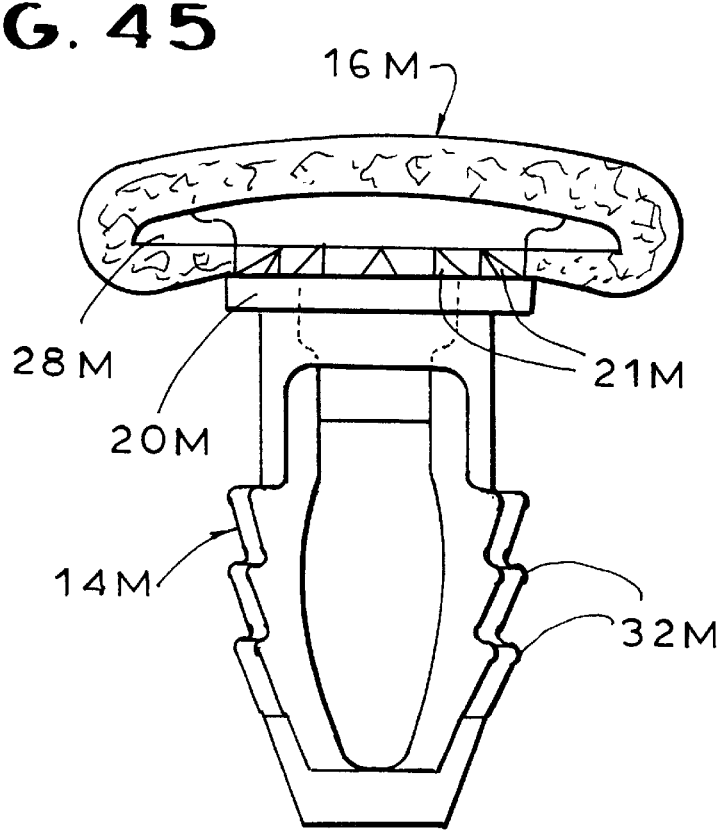
FIG. 45 is a side elevational view, partially in section, of the fourteenth embodiment.

Either through a lack of surgical skill or, in certain instances, intentionally (e.g., where the depth of the cancellous bone is insufficient to provide suitable anchoring for the delivery unit when inserted at a suitable angle to properly position the insert), off-axis placement of the shaft or stem of delivery unit may result in a non-flush curvature of the top of the insert with the adjacent healthy cartilage. Referring now to FIG. 45, the present invention therefore additionally encompasses a fourteenth embodiment 10P which has a delivery unit 14P with a shaft or stem 80P and a swivel or pivotable head 82P. The distal end of the delivery unit shaft 80P defines a ball or ball-like surface 84P, and the proximal end of the delivery unit head 82P defines a socket or socket-like surface 86P adapted to receive and retain the ball 84P. The insert 16P is wrapped around the delivery unit head 82P and secured thereto by a retainer ring 20P or like structure performing the same function. Thus, if the delivery unit shaft 80P has been inserted into the cancellous bone at an angle such that the insert 16P within the head portion 82P is not aligned with the cartilage surface—either through accident or intentionally—the delivery unit head 82P may be swivelled or pivoted relative to the delivery unit shaft 80P, thereby enabling the insert 16P to be aligned with the healthy articular cartilage surface while the shaft 80P is fixedly retained in the cancellous bone. Preferably the distal end of the delivery unit shaft 80P and the proximal end of the delivery unit head 82P are beveled to permit head inclinations of at least 15 degrees in either direction, and the removed cartilage and bone area is large enough to accommodate such swivelling. It will be appreciated that this swivel head or ball-and-socket embodiment 10P enables the assembly of the present invention to be utilized even where the cancellous bone is inadequate in depth to receive a delivery unit shaft extending normal thereto, as the delivery unit shaft may be implanted in the cancellous bone at a non-normal or inclined angle so as to make maximum use of the available bone, and the delivery unit head then swivelled (relative to the delivery unit shaft) to provide an optimum orientation relative to the remaining cartilage.

Each of the several embodiments shown and described herein includes particular structural features and offers particular functional advantages. As will be apparent to those skilled in the art, the particular structural features and the particular functional advantages of one given embodiment may generally be used in conjunction with another embodiment to provide that other embodiment with the same or like structural features and functional advantages. By way of example, in general the retainer means of one embodiment may be substituted for the retainer means of another embodiment, and the delivery unit of one embodiment may be substituted for the delivery unit of another embodiment.

Further, one embodiment of the present invention encompasses a cartilage and bone repair system to be mounted both in an area of damaged or destroyed articular cartilage and damaged subchondral bone, and an adjacent healthy area of articular cartilage and cancellous; bone. The system comprises an assembly of a bio-absorbable delivery unit and a porous bio-absorbable insert. The delivery unit is formed of bio-absorbable material. The delivery unit has a central body and a plurality of radially extending support arms projecting outwardly from the central body and configured to support the insert. The insert is supported by the delivery unit, is formed of bio-absorbable materials and establishes communication between the removed area of bone and cartilage and the adjacent healthy area for a chondrogenic and osteogenic growth supporting matrix. The matrix may be one layer or a bilayer where the lower layer is designed to create an osteogenic supporting matrix and the upper layer is designed to create a chondrogenic supporting matrix. indeed even a single layer matrix may function as a bilayer—e.g., when the upper portion is pre-dipped in a liquid chondrogenic support and the lower portion is pre-dipped in a liquid osteogenic support.

In a further embodiment each layer could be impregnated as appropriate with chondrogenic repair factors or osteogeneric repair factors including demineralized bone, BMP's, TCP, TAFB, etc.

To summarize, the present invention provides a system for regenerating articular cartilage wherein the regenerated articular cartilage is functionally similar to non-damaged articular cartilage and therefore replaces damaged or destroyed articular cartilage without employing cement or a non bio-absorbable prosthetic device.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

We claim:

1. A bio-absorbable cartilage repair system for regenerating damaged or destroyed articular cartilage on a joint surface of a bone by establishing a chondrogenic growth-supporting matrix between an area of damaged or destroyed articular cartilage that has been removed and an adjacent healthy area of articular cartilage and subchondral cancellous bone, said system comprising a delivery unit and a porous insert;

(A) said delivery unit being formed of bio-absorbable material and configured and dimensioned to be mounted in both an area of damaged or destroyed articular cartilage that has been removed and an adjacent healthy area of articular cartilage and cancellous bone, said delivery unit having a central body and a plurality of radially extending, flexible support arms projecting outwardly from said central body and configured and dimensioned to support said insert; and (B) said insert being formed of bio-absorbable material and establishing communication between the removed area and the adjacent healthy area for a chondrogenic growth-supporting matrix.

2. The system of claim 1 wherein said support arms have upper, lower, and outer surfaces and wherein said insert is disposed on the upper, lower and outer surfaces of said support arms.

3. The system of claim 1 wherein said support arms have free ends circumferentially spaced from one another to define areas for receipt of a chondrogenic growth-supporting matrix.

4. The system of claim 1 wherein said support arms have circumferentially spaced free ends adapted to engage and at least partially spatially stabilize said insert.

5. The system of claim 1 wherein said support arms have free ends and wherein the free ends are horizontally barbed.

6. The system of claim 1 wherein said support arm free ends are vertically barbed.

7. The system of claim 1 wherein said insert has a top, a bottom and a sidewall connecting said top and bottom, said bottom allowing vascular invasion therethrough, and said top and sidewall allowing cellular migration.

8. The system of claim 7 wherein said sidewall is polygonal in plan.

9. The system of claim 7 wherein said sidewall is circular in plan.

10. The system of claim 1 wherein each of said delivery unit and said insert essentially consist of completely bio-absorbable material which is dimensionally stable in synovial joint fluid against expansion due to the absorption thereof.

11. The system of claim 1 additionally including retainer means securing said insert to said delivery unit.

12. The system of claim 11 wherein said retainer means is secured to a portion of said central body below said insert and bears upwardly against said insert.

13. The system of claim 11 wherein said retainer means essentially consists of completely bio-absorbable material which is dimensionally stable in synovial joint fluid against expansion due to the absorption thereof.

14. The system of claim 1 comprising a porous film formed of bio-absorbable material securing said insert to said delivery unit.

15. The system of claim 14 wherein said porous film has a central film portion disposed over said insert and a plurality of film fingers projecting outwardly from said central film portion, downwardly and inwardly, under said support arms.

16. The system of claim 15 comprising retainer means secured to a lower part of said central body and bearing upwardly against said film fingers.

17. The system of claim 14 wherein said porous film essentially consists of completely bio-absorbable material which is dimensionally stable in synovial joint fluid against expansion due to the absorption thereof.

18. The system of claim 1 wherein said central body comprises a plurality of outwardly extending flanges.

19. The system of claim 1 wherein said insert is a flexible porous film formed of bio-absorbable material secured to said delivery unit.

20. The system of claim 19 wherein said porous film has a central film portion disposed over said support arms and a plurality of film fingers projecting outwardly from said central film portion, downwardly and inwardly, under said support arms.

21. The system of claim 20 additionally including retainer means secured to a lower part of said central body and bearing upwardly against said film fingers.

22. The system of claim 19 wherein said porous film essentially consists of completely bio-absorbable material which is dimensionally stable in synovial joint fluid against expansion due to the absorption thereof.

23. The system of claim 1 wherein said central body defines an aperture extending longitudinally therethrough.

24. The system of claim 23 wherein said insert defines an aperture extending longitudinally therethrough.

25. The system of claim 23 additionally including retainer means secured to a lower part of said central body and bearing upwardly against said insert, said retainer body defining an aperture extending longitudinally therethrough coaxial with said central body aperture.

26. The system of claim 23 additionally including a porous film consisting substantially of completely bio-absorbable material securing said insert to said delivery unit, said porous film defining an aperture extending, longitudinally therethrough coaxial with said central body aperture.

27. The system of claim 23 wherein said insert is a flexible porous film consisting substantially of completely bio-absorbable material secured to said delivery unit, said porous film defining an aperture extending longitudinally therethrough coaxial with said central body aperture.

28. The system of claim 1 wherein at least a portion of said delivery unit central body disposed below said insert defines flexible legs, said system additionally including means for moving said legs from a horizontally retracted orientation enabling removal of said assembly to a horizontally expanded orientation fixing said assembly in place.

29. The system of claim 28 wherein said flexible legs are resilient, and said moving means is retractable to enable movement of said legs from said expanded orientation to said retracted orientation.

30. The system of claim 1 wherein said insert includes cartilage or cartilage-progenitor cells to facilitate establishing said communication.

31. The system of claim 1 wherein said delivery unit is provided by two separately formed components, one of said components being configured and dimensioned to be mounted in both an area of damaged or destroyed articular cartilage that has been removed and an adjacent healthy area of articular cartilage and cancellous bone, and the other component providing the central body and plurality of radially extending, flexible support arms projecting outwardly from said central body and configured and dimensioned to support said insert.

32. The system of claim 31 wherein said delivery unit includes retainer means for bearing on a portion of said insert intermediate said two components to lock said insert portion in place.

33. The system of claim 31 wherein said delivery unit is assembled with said insert prior to use.

34. The system of claim 31 wherein said one component defines a longitudinal aperture therethrough, and said central body of said other component is configured and dimensioned to at least partially pass through said aperture.

35. The system of claim 31 wherein at least one of said components includes means for retaining said components together after assembly.

36. A bio-absorbable cartilage repair system for regenerating damaged or destroyed articular cartilage on a joint surface of a bone by establishing a chondrogenic growth-supporting matrix between an area of damaged or destroyed articular cartilage that has been removed and an adjacent healthy area of articular cartilage and subchondral cancellous bone, said system consisting essentially of two delivery units and a single flexible porous insert;

(A) each of said delivery units being formed of bio-absorbable material and configured and dimensioned to be mounted in both an area of damaged or destroyed articular cartilage that has been removed and an adjacent healthy area of articular cartilage and cancellous bone, each said delivery unit having a central body and a plurality of radially extending, flexible support arms projecting outwardly from said central body and configured and dimensioned to support said insert; and (B) said insert being formed of flexible bio-absorbable material and establishing communication between the removed area and the adjacent healthy area for a chondrogenic growth-supporting matrix;

said delivery units being configured and dimensioned to enable them to be disposed facing each other and connected only by said insert for insertion into a patient and then unfolded to enable them to be separately mounted side-by-side.

37. The system of claim 36 wherein said insert defines a pair of insert portions, each said insert portion extending over the top of a respective one of said delivery units, and a connecting portion of reduced width foldably connecting said insert portions together.

38. A bio-absorbable cartilage repair system for regenerating damaged or destroyed articular cartilage on a joint surface of a bone by establishing a chondrogenic growth-supporting matrix between an area of damaged or destroyed articular cartilage that has been removed and an adjacent healthy area of articular cartilage and subchondral cancellous bone, said system comprising a delivery unit and a porous insert;

(A) said delivery unit being formed of bio-absorbable material and configured and dimensioned to be mounted in both an area of damaged or destroyed articular cartilage that has been removed and an adjacent healthy area of articular cartilage and cancellous bone, said delivery unit having a central body and a plurality of inwardly compressible flexible support arms projecting outwardly from said central body and configured and dimensioned to support said insert; and (B) said insert being formed of bio-absorbable material and establishing communication between the removed area and the adjacent healthy area for a chondrogenic growth-supporting matrix.

39. The system of claim 38 comprising at least two of said delivery units, each said delivery unit being mounted side-by-side such that at least one support arm of one of said delivery units inwardly compresses at least one support arm of the other of said delivery units.

40. The system of claim 39 wherein said at least one support arm of said one delivery unit would overlap said at least one support arm of said other delivery unit if at least one of the support arms was not inwardly compressed.

41. The system of claim 39 wherein said insert and said support arms are deflectable.

42. The system of claim 1 wherein a top layer of said insert contains a chondrogenic growth-supporting matrix and a lower portion of said insert contains an osteogenic growth-supporting matrix, the insert configured and dimensioned to be disposed with said chondrogenic growth-supporting matrix adjacent a healthy area of articular cartilage and said osteogenic growth-supporting matrix adjacent a healthy area of subchondral cancellous bone, thereby establishing chondrogenic and osteogenic growth-supporting matrices in removed areas of damaged or destroyed articular cartilage and subchondral bone, respectively.

43. A bio-absorbable cartilage repair system for regenerating damaged or destroyed articular cartilage on a joint surface of a bone by establishing a chondrogenic growth-supporting matrix between an area of damaged or destroyed articular cartilage that has been removed and an adjacent healthy area of articular cartilage and subchondral cancellous bone, said system comprising an assembly of a delivery unit and a porous insert;

(A) said delivery unit being formed of bio-absorbable material and configured and dimensioned to be mounted in both an area of damaged or destroyed articular cartilage that has been removed and an adjacent healthy area of articular cartilage and cancellous bone, said delivery unit having a central body and a plurality of radially extending, flexible support arms projecting outwardly from said central body and configured and dimensioned to support said insert;

(B) said insert being formed of bio-absorbable material and establishing communication between the removed area and the adjacent healthy area for a chondrogenic growth-supporting matrix; and said delivery unit including a head portion and a stem portion, said head and stem portions being pivotally joined together.

44. The system of claim 43 wherein one of said portions defines a ball and the other of said portions defines a socket.

45. The system of claim 44 wherein said stem portion defines a ball at a distal end, and said head portion defines a socket at a proximal end, said ball being pivotally maintained in said socket such that said head portion is pivotable relative to said stem portion.

* * * * *